United States Patent
Hussain et al.

(10) Patent No.: US 11,866,641 B2
(45) Date of Patent: *Jan. 9, 2024

(54) METHOD FOR FRACKING SUBTERRANEAN GEOLOGICAL FORMATION WITH SURFACTANT-CONTAINING FLUID

(71) Applicant: KING FAHD UNIVERSITY OF PETROLEUM AND MINERALS, Dhahran (SA)

(72) Inventors: S. M. Shakil Hussain, Dhahran (SA); Muhammad Shahzad Kamal, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/146,205

(22) Filed: Dec. 23, 2022

(65) Prior Publication Data

US 2023/0138419 A1  May 4, 2023

Related U.S. Application Data

(63) Continuation of application No. 16/749,342, filed on Jan. 22, 2020, now Pat. No. 11,555,143.

(60) Provisional application No. 62/910,856, filed on Oct. 4, 2019.

(51) Int. Cl.

| | | |
|---|---|---|
| C09K 8/68 | (2006.01) | |
| C09K 8/584 | (2006.01) | |
| C07C 229/12 | (2006.01) | |
| C07C 305/04 | (2006.01) | |
| C09K 8/06 | (2006.01) | |
| C07C 305/10 | (2006.01) | |

(52) U.S. Cl.
CPC ............ *C09K 8/584* (2013.01); *C07C 229/12* (2013.01); *C07C 305/04* (2013.01); *C07C 305/10* (2013.01); *C09K 8/06* (2013.01); *C09K 8/68* (2013.01)

(58) Field of Classification Search
CPC . C09K 8/584; C09K 8/06; C09K 8/68; C09K 8/602; C09K 8/035; C09K 8/86; C07C 229/12; C07C 305/04; C07C 305/10; C07C 235/10; C07C 309/14
See application file for complete search history.

(56) References Cited

U.S. PATENT DOCUMENTS 3,759,981 A 9/1973 Hager
4,913,841 A 4/1990 Zeman

2004/0074650 A1 4/2004 Shiga
2004/0163307 A1* 8/2004 Dahlmann ......... C08G 65/3311
44/405
2018/0112122 A1 4/2018 Phan

FOREIGN PATENT DOCUMENTS

| CN | 101745343 A | 6/2010 |
|---|---|---|
| CN | 102974268 A | 3/2013 |
| WO | WO 2009058589 A2 | 5/2009 |
| WO | WO 2009058589 A3 | 5/2009 |

OTHER PUBLICATIONS

Hussain (S.M.S. Hussain, et al., Synthesis and physicochemical investigation of betaine type polyoxyethylene zwitterionic surfactants containing different ionic headgroups, Journal of Molecular Structure 1178 (2019) 83-88).*
S.M. Shakil Hussain, et al., "Synthesis and physicochemical investigation of betaine type polyoxyethylene zwitterionic surfactants containing different ionic headgroups", Journal of Molecular Structure, vol. 1178, Feb. 2019, pp. 83-88 (Abstract only).
S.M. Shakil Hussain, et al., "Synthesis and performance evaluation of betaine type zwitterionic surfactants containing different degrees of ethoxylation", Journal of Molecular Structure, vol. 1173, Dec. 2018, pp. 983-989 (Abstract only).
Muhammad Shahzad Kamal, et al., "Development of Polyoxyethylene Zwitterionic Surfactants for High-Salinity High-Temperature Reservoirs", Journal of Surfactants and Detergents, vol. 22, Issue 4, Mar. 21, 2019, pp. 795-806 (Abstract only).
Muhammad Shahzad Kamal, et al., "A Zwitterionic Surfactant Bearing Unsaturated Tail for Enhanced Oil Recovery in High-Temperature High-Salinity Reservoirs", Journal of Surfactants and Detergents, vol. 21, Issue 1, Feb. 21, 2018, pp. 165-174 (Abstract only).
Hong-yan Cai, et al., "Preparation and properties of oleyl amidopropyl betaine", China Surfactant Detergent & Cosmetics, Jun. 2013, 2 pages (Abstract only).

(Continued)

*Primary Examiner* — Kumar R Bhushan
(74) *Attorney, Agent, or Firm* — Oblon, McClelland, Maier & Neustadt, L.L.P.

(57) ABSTRACT

A surfactant of formula (I)

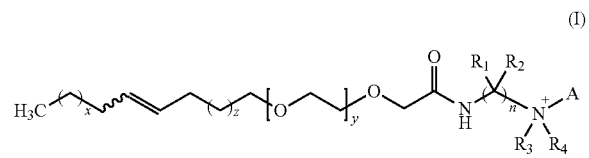

wherein each of $R_1$ and $R_2$ are independently a hydrogen, an optionally substituted alkyl, an optionally substituted cycloalkyl, or an optionally substituted arylalkyl, $R_3$ and $R_4$ are independently an optionally substituted alkyl, an optionally substituted cycloalkyl, or an optionally substituted arylalkyl, x is an integer in a range of 2-8, y is an integer in a range of 1-15, z is an integer in a range of 4-10, n is an integer in a range of 2-5, and A is one of a carboxybetaine group, a sulfobetaine group, or a hydroxy sulfobetaine group. An oil and gas well servicing fluid containing the surfactant and methods of servicing an oil and gas well are also described.

15 Claims, 6 Drawing Sheets

(56) References Cited

OTHER PUBLICATIONS

Peiqian Li, et al., "A New Type of Sulfobetaine Surfactant with Double Alkyl Polyoxyethylene Ether Chains for Enhanced Oil Recovery", Journal of Surfactants and Detergents, vol. 19, Issue 5, Sep. 2016, pp. 967-977 (Abstract only).

Document (https://drugs.ncats.io/drug/172F2WN8DV, downloaded on Aug. 12, 2022).

* cited by examiner

METHOD FOR FRACKING SUBTERRANEAN GEOLOGICAL FORMATION WITH SURFACTANT-CONTAINING FLUID

CROSS REFERENCE TO RELATED APPLICATIONS

This application is a Continuation of U.S. application Ser. No. 16/749,342, now allowed, having a filing date of Jan. 22, 2020 which claims benefit of priority to U.S. Provisional Application No. 62/910,856 having a filing date of Oct. 4, 2019.

STATEMENT OF ACKNOWLEDGEMENT

This research was supported by the College of Petroleum Engineering & Geoscience, KFUPM through project no. SF-17003.

STATEMENT REGARDING PRIOR DISCLOSURE BY THE INVENTORS

Aspects of this technology are described in an article "Synthesis and physicochemical investigation of betaine type polyoxyethylene zwitterionic surfactants containing different ionic headgroups" published in Journal of Molecular Structure, 2019, 1178, 83-88, available online on Oct. 5, 2018, which is incorporated herein by reference in its entirety.

BACKGROUND OF THE INVENTION

Technical Field

The present disclosure relates to betaine-type surfactants containing an unsaturated fatty tail, servicing fluids made therefrom, and methods of using the surfactants in oil and gas well servicing operations.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Surfactants are composed of hydrophilic (the "head") and hydrophobic (the "tail") groups and are soluble in organic solvents and water. See A. H. Abbas, W. R. W. Sulaiman, M. Z. Jaafar, A. A. Olayink, S. S. Ebrahimi, A. Elrufai, Numerical study for continuous surfactant flooding considering adsorption in heterogeneous reservoir, Journal of King Saud University-Engineering Sciences (2018), incorporated herein by reference in its entirety. They are known to reduce the surface tension and interfacial tension (IFT) between crude oil and water, increase the capillary number, alter the wettability of reservoir rocks towards more water wet, ultimately enhancing the efficiency of oil production. See A. M. Howe, A. Clarke, J. Mitchell, J. Staniland, L. Hawkes, C. Whalan, Visualising surfactant enhanced oil recovery, Colloids and Surfaces A: Physicochemical and Engineering Aspects 480 (2015) 449-461, incorporated herein by reference in its entirety. However, use of surfactants in upstream applications is challenging owing to poor thermal stability, poor solubility, and high adsorption of the surfactants on the formation rocks. See P. Raffa, A. A. Broekhuis, F. Picchioni, Polymeric surfactants for enhanced oil recovery: A review, Journal of Petroleum Science and Engineering 145 (2016) 723-733; N. Saxena, N. Pal, S. Dey, A. Mandal, Characterizations of surfactant synthesized from palm oil and its application in enhanced oil recovery, Journal of the Taiwan Institute of Chemical Engineers 81 (2017) 343-355; N. Pal, N. Saxena, K. D. Laxmi, A. Mandal, Interfacial behaviour, wettability alteration and emulsification characteristics of a novel surfactant: Implications for enhanced oil recovery, Chem. Eng. Sci. (2018); and N. Pal, N. Saxena, A. Mandal, Studies on the physicochemical properties of synthesized tailor-made gemini surfactants for application in enhanced oil recovery, J. Mol. Liq. (2018), each incorporated herein by reference in their entirety.

Surfactants can be categorized as nonionic, zwitterionic, anionic, and cationic depending on the charge of the headgroup, which contributes to the physicochemical properties of surfactants. See G. Wu, C. Yuan, X. Ji, H. Wang, S. Sun, S. Hu, Effects of head type on the stability of gemini surfactant foam by molecular dynamics simulation, Chemical Physics Letters 682 (2017) 122-127, incorporated herein by reference in its entirety. The selection of a suitable class of surfactant largely depends on the nature of reservoir rocks. See K. Ma, L. Cui, Y. Dong, T. Wang, C. Da, G. J. Hirasaki, S. L. Biswal, Adsorption of cationic and anionic surfactants on natural and synthetic carbonate materials, Journal of colloid and interface science 408 (2013) 164-172, incorporated herein by reference in its entirety. For instance, anionic surfactants are typically preferred for sandstone rocks due to low adsorption. See W. Kwok, R. Hayes, H. Nasr-El-Din, Modelling dynamic adsorption of an anionic surfactant on Berea sandstone with radial flow, Chemical engineering science 50(5) (1995) 769-783, incorporated herein by reference in its entirety. Similarly, cationic surfactants are often applied in carbonate reservoirs in order to avoid high adsorption. See S. S. Hussain, M. S. Kamal, Effect of large spacer on surface activity, thermal, and rheological properties of novel amido-amine cationic gemini surfactants, Journal of Molecular Liquids 242 (2017) 1131-1137, incorporated herein by reference in its entirety. Moreover, nonionic surfactants are used to enhance salt tolerance, but they show higher IFT values compared to anionic surfactants.

Zwitterionic surfactants have gained considerable attention both in the academic field and industry due to superior properties such as heat resistance, salt tolerance, excellent aqueous solubility, high foam stability, and good biodegradability. See S. j. Dong, Y. l. Li, Y. b. Song, L. f. Zhi, Synthesis, Characterization and Performance of Unsaturated Long-Chain Carboxybetaine and Hydroxy Sulfobetaine, Journal of Surfactants and Detergents 16(4) (2013) 523-529, incorporated herein by reference in its entirety. A number of zwitterionic surfactants have been devised for oilfield applications and the number continues to increase. See A. Kumar, A. Mandal, Characterization of rock-fluid and fluid-fluid interactions in presence of a family of synthesized zwitterionic surfactants for application in enhanced oil recovery, Colloids and Surfaces A: Physicochemical and Engineering Aspects 549 (2018) 1-12; S. S. Hussain, M. S. Kamal, L. T. Fogang, Effect of internal olefin on the properties of betaine-type zwitterionic surfactants for enhanced oil recovery, J. Mol. Liq. (2018); S. Chen, H. Liu, H. Sun, X. Yan, G. Wang, Y. Zhou, J. Zhang, Synthesis and physiochemical performance evaluation of novel sulphobetaine zwitterionic surfactants from lignin for enhanced oil recovery, Journal of Molecular Liquids 249 (2018) 73-82; and C. Da, S. Alzobaidi, G. Jian, L. Zhang, S. L. Biswal, G. J. Hirasaki, K. P. Johnston, Carbon dioxide/water foams stabilized with a zwitterionic surfactant at temperatures up to 150° C. in high salinity brine, Journal of Petroleum Science and Engineering 166 (2018) 880-890, each incorporated herein by reference in their entirety.

The functionality and overall chemical structure of zwitterionic surfactants plays a key role for selected oilfield applications. For example, the addition of a carboxylate head group may enhance the water solubility of the surfactant, and the introduction of a hydroxy sulfobetaine head group increases hydrophilicity. See Y. Wang, Y. Zhang, X. Liu, J. Wang, L. Wei, Y. Feng, Effect of a Hydrophilic Head Group on Krafft Temperature, Surface Activities and Rheological Behaviors of Erucyl Amidobetaines, J. Surfactants. Deterg. 17(2) (2014) 295-301, incorporated herein by reference in its entirety. However, the increase in chain length lowers the water solubility of the surfactant. Long hydrophobic tails (≥C18) have shown the ability to form wormlike micelles, but their poor water solubility has limited surfactants to hydrophobic tails made from less than 18 carbon atoms. See S. Shakil Hussain, M. A. Animashaun, M. S. Kamal, N. Ullah, I. A. Hussein, A. S. Sultan, Synthesis, characterization and surface properties of amidosulfobetaine surfactants bearing odd-number hydrophobic tail, Journal of Surfactants and Detergents 19(2) (2016) 413-420, incorporated herein by reference in its entirety. This poor solubility may be at least partially offset through the introduction of ethoxylated (EO) units, which may also improve thermal stability, and prevent the need for co-solvents such as alcohol to attain ultralow IFT values. See B. Barry, R. Wilson, CMC, counterion binding and thermodynamics of ethoxylated anionic and cationic surfactants, Colloid and Polymer Science 256(3) (1978) 251-260; C. Negin, S. Ali, Q. Xie, Most common surfactants employed in chemical enhanced oil recovery, Petroleum 3(2) (2017) 197-211, each incorporated herein by reference in its entirety. However, an improperly chosen degree of ethoxylation can lead to low recovery, high adsorption onto the reservoir rocks and/or possible rock dissolution resulting in formation damage. With so many competing issues, it is difficult to predict how a particular surfactant will fair in a specified oil field application/setting. Therefore, developing surfactants that reduce the IFT between crude oil and water, are thermally stable under reservoir conditions, are soluble in high salinity environments, and which provide low adsorption into formation rocks, remains a significant challenge.

In view of the forgoing, one objective of the present disclosure is to provide betaine-type surfactants containing an unsaturated fatty tail which overcome these challenges. Another objective of the present disclosure is to provide servicing fluids containing these surfactants for use in servicing oil and gas wells.

BRIEF SUMMARY OF THE INVENTION

According to a first aspect, the present disclosure relates to a surfactant of formula (I)

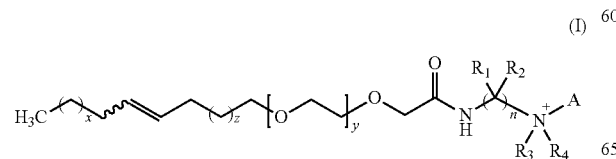

wherein:
each of $R_1$ and $R_2$ are independently selected from the group consisting of a hydrogen, an optionally substituted alkyl, an optionally substituted cycloalkyl, and an optionally substituted arylalkyl;
$R_3$ and $R_4$ are independently selected from the group consisting of an optionally substituted alkyl, an optionally substituted cycloalkyl, and an optionally substituted arylalkyl;
x is an integer in a range of 2-8;
y is an integer in a range of 1-15;
z is an integer in a range of 4-10;
n is an integer in a range of 2-5;
A is an anionic headgroup selected from the group consisting of

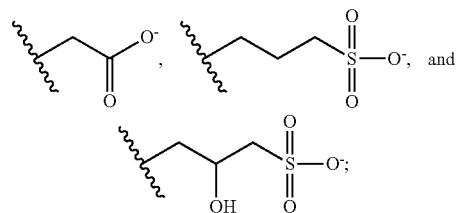

or a solvate, tautomer thereof, or stereoisomer thereof.

In some embodiments, each of $R_1$ and $R_2$ are independently a hydrogen, or a methyl.

In some embodiments, each of $R_1$ and $R_2$ are a hydrogen.

In some embodiments, $R_3$ and $R_4$ are independently selected from the group consisting of a methyl, an ethyl, and an isopropyl.

In some embodiments, $R_3$ and $R_4$ are a methyl.
In some embodiments, x is an integer in a range of 4-6.
In some embodiments, y is an integer in a range of 7-10.
In some embodiments, z is 6.
In some embodiments, n is 3.
In some embodiments, A is

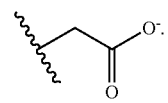

In some embodiments, A is

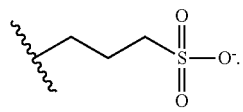

In some embodiments, A is

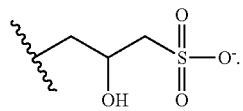

In some embodiments, the carbon-carbon double bond present in formula (I) is in a cis-double bond configuration.

In some embodiments, the surfactant is selected from the group consisting of

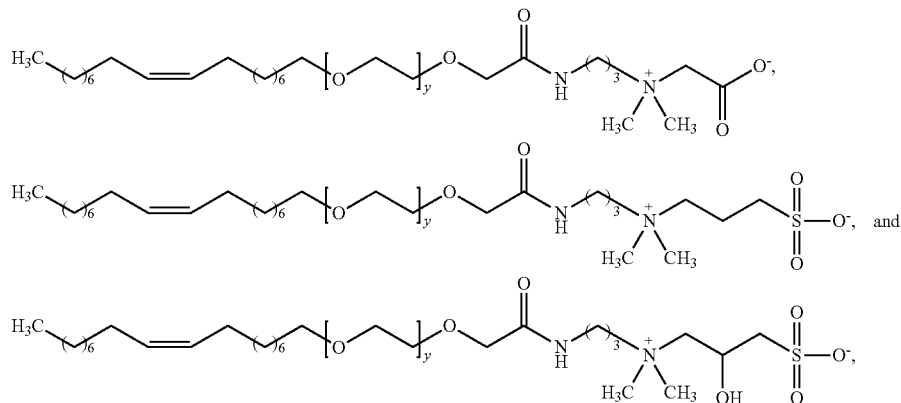

wherein in each structure y is 8 or 9.

In some embodiments, the surfactant has a critical micelle concentration in water at 30 to 60° C. of $3 \times 10^{-5}$ to $5 \times 10^{-4}$ M, and a surface tension at the critical micelle concentration of 31-39 mN/m.

According to a second aspect, the present disclosure relates to an oil and gas well servicing fluid, containing an aqueous base fluid and the surfactant of formula (I).

In some embodiments, the oil and gas well servicing fluid has a total dissolved solids content of 50,000-350,000 ppm.

In some embodiments, the surfactant is present in an amount of 0.001-15 wt. % relative to a total weight of the oil and gas well servicing fluid.

According to a third aspect, the present disclosure relates to a method of servicing an oil and gas well during fracking, drilling, completion, and/or workover whereby the oil and gas well servicing fluid is injected into the oil and gas well.

In some embodiments, the oil and gas well has a temperature of 30-150° C.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
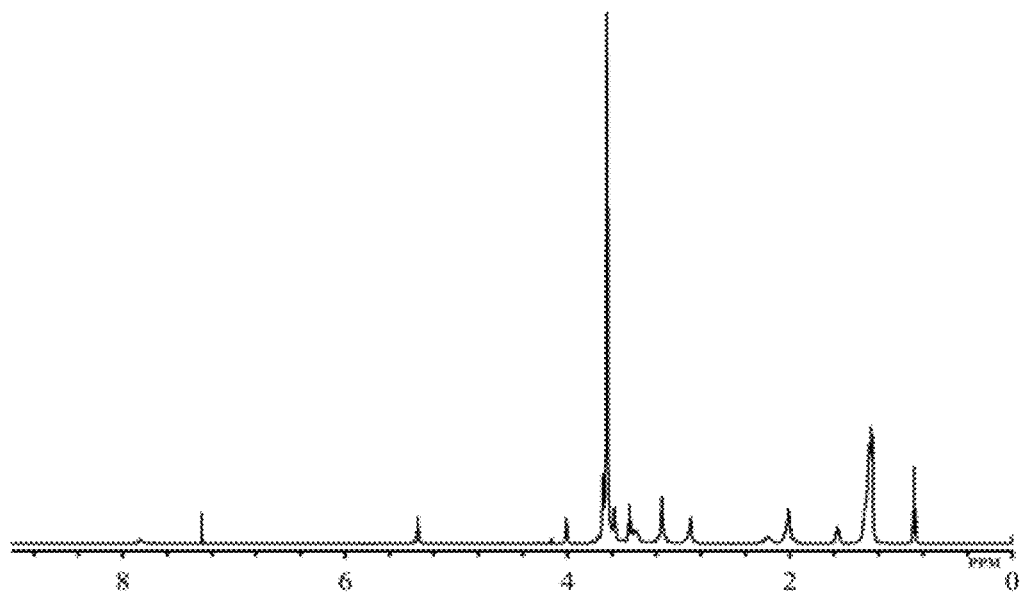
FIG. 1 illustrates the $^1$H NMR spectra of OPAS.

Embodiments of the present disclosure will now be described more fully hereinafter with reference to the accompanying drawings, in which some, but not all embodiments of the disclosure are shown.

Definitions

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, yet even more preferably 0 wt. %, relative to a total weight of the composition being discussed.

As used herein, the terms "optional" or "optionally" means that the subsequently described event(s) can or cannot occur or the subsequently described component(s) may or may not be present (e.g., 0 wt. %).

As used herein, the terms "compound", "surfactant", and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C═C double bonds, C═N double bonds, ring systems, and the like can also be present in the compounds, and all such stable isomers are contemplated in the present disclosure. Cis- and trans- (or Z- and E-) geometric isomers of the compounds of the present disclosure, which may be denoted by using undefined bond geometries, e.g.,

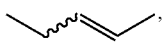

are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, aryl sulfonyl, arylalkylsulfonyl, sulfonamide (e.g. —SO$_2$NH$_2$), substituted sulfonamide, nitro, cyano, carboxy, unsubstituted amide (i.e. —CONH$_2$), substituted amide (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those of ordinary skill in the art, for example, as taught in Greene, et al., "Protective Groups in Organic Synthesis", John Wiley and Sons, Second Edition, 1991, hereby incorporated by reference in its entirety.

As used herein, the term "alkyl" or "alkylene" unless otherwise specified refers to both branched and straight-chain saturated aliphatic primary, secondary, and/or tertiary hydrocarbons having a specified number of carbon atoms. For example, "C$_1$ to C$_6$ alkyl" or "C$_{1-6}$ alkyl" (or alkylene) denotes alkyl chain having 1 to 6 carbon atoms. The alkyl or alkylene groups typically include C$_1$ to C$_{21}$, for example C$_1$, C$_2$, C$_3$, C$_4$, C$_5$, C$_6$, C$_7$, C$_8$, C$_9$, C$_{10}$, C$_{11}$, C$_{12}$, and specifically includes, but is not limited to, methyl, trifluoromethyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, 2,3-dimethylbutyl, 2-ethylhexyl, n-heptyl, n-octyl, n-nonyl, 3,7-dimethyloctyl, n-decyl, n-undecyl, n-dodecyl, n-tridecyl, and 2-propylheptyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "aryl", as used herein, and unless otherwise specified, refers to a substituent that is derived from an aromatic hydrocarbon (arene) that has had a hydrogen atom removed from a ring carbon atom. Aryl includes phenyl, biphenyl, naphthyl, anthracenyl, and the like.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "halide", as used herein, means fluoride, chloride, bromide, and iodide.

The term "halogen", as used herein, means fluoro, chloro, bromo and iodo.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, and isotopes of oxygen include $^{16}O$, $^{17}O$ and $^{18}O$. Isotopically labeled compounds of the disclosure can generally be prepared by conventional techniques known to those of ordinary skill in the art or by processes and methods analogous to those described herein, using an appropriate isotopically labeled reagent in place of the non-labeled reagent otherwise employed.

For purposes of clarity and in accordance with standard convention in the art, the symbol

is used in formulas to show the bond that is the point of attachment of the moiety or substituent to the core/nucleus of the structure.

As used herein, "formation water" is native water (connate and interstitial water) present in a subterranean formation.

As used herein, "oil and gas well servicing fluid" (or servicing fluid) means water plus any solids, liquids, and/or gasses entrained therein that is injected into a subterranean formation during various drilling operations. Examples of oil and gas well servicing fluids include, but are not limited to, fracking fluids, drilling fluids, completion fluids, and workover fluids.

"Fracking fluid" (or frac fluid) is an injectable fluid used in fracking operations to increase the quantity of hydrocarbons that can be extracted. Fracking fluids contain primarily water, and may contain proppants (e.g., sand) and other desirable chemicals for modifying well production and fluid properties.

"Drilling fluid" is a circulated fluid system that is used to aid the drilling of boreholes, for example, to provide hydrostatic pressure to prevent formation fluids from entering into the wellbore, to keep the drill bit cool and clean during drilling, to carry out drill cuttings, and/or to suspend the drill cuttings while drilling is paused and when the drilling assembly is brought in and out of the hole.

"Completion fluid" is a circulated fluid system that is used to complete/clean an oil or gas well, i.e., to facilitate final operations prior to initiation of production, such as setting screens production liners, packers, downhole valves or shooting perforations into the producing zone. Completion fluids are typically solids-free brines meant to control a well should downhole hardware fail, without damaging the producing formation or completion components.

"Workover fluid" is a circulated fluid system that is used during workover operations, i.e., to repair or stimulate an existing production well for the purpose of restoring, prolonging, and/or enhancing the production of hydrocarbons therefrom, and includes stimulation fluids used in acidizing for example.

As used herein, "wastewater" means a water source obtained from storm drains, sedimentation ponds, runoff/outflow, landfills, as well as water sources resulting/obtained from industrial processes such as factories, mills, farms, mines, quarries, industrial drilling operations, oil and gas recovery operations, papermaking processes, food preparation processes, phase separation processes, washing processes, waste treatment plants, toilet processes, power stations, incinerators, spraying and painting, or any other manufacturing or commercial enterprise, which comprises water and one or more compounds or materials derived from such industrial processes, including partially treated water from these sources.

As used herein, "produced water", a particular type of wastewater, refers to water that flows back from a subterranean formation in a hydrocarbon recovery process and comprises one or more natural formation fluids such as formation water, sea water, and hydrocarbon, and optionally any fluid that has been injected into the subterranean formation during various drilling operations.

Surfactant

Surfactants are widely used in the oil and gas industry during various stages of upstream (exploration, field development, and production operations) and midstream (transportation e.g., by pipeline, processing, storage, and distribution) oil recovery operations. The surfactants of the present disclosure are intended to be useful as a general surfactant in any of these various stages, and may be added to fracking fluids, drilling fluids, completion fluids, workover fluids, among others, for use for example during drilling, cementing, fracturing, acidizing, demulsification, corrosion inhibition, cleaning, flooding (e.g., waterflooding, chemical flooding, foam and steam flooding), enhanced oil recovery, transportation, and the like. In particular, the surfactants of the present disclosure are suitable for challenging reservoir conditions, such as those where high total dissolved solids (TDS) contents and high temperatures are encountered.

According to a first aspect, the present disclosure thus provides a surfactant of formula (I)

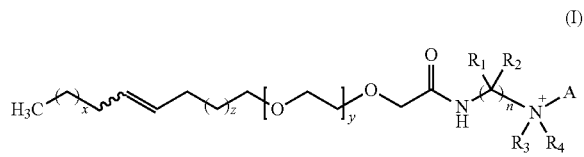

or a solvate, tautomer thereof, or stereoisomer thereof. The different moieties present within formula (I) are carefully coordinated in order to achieve excellent surface properties, solubility in high salinity brines, and thermal stability. For instance, the amide group [—(O)C—NH—] is thought to advantageously provide low cmc, good biodegradability, and environmentally friendliness (lower toxicity). See K. Taleb, M. Mohamed-Benkada, N. Benhamed, S. Saidi-Besbes, Y. Grohens, A. Derdour, Benzene ring containing cationic gemini surfactants: Synthesis, surface properties and antibacterial activity, J. Mol. Liq. 241 (2017) 81-90, incorporated herein by reference in its entirety. Similarly, the unsaturated fatty tail is thought to contribute to low cmc because of rigidity in the hydrophobic tail. See M.-T. Lee, A. Vishnyakov, A. V. Neimark, Calculations of critical micelle concentration by dissipative particle dynamics simulations: the role of chain rigidity, The Journal of Physical Chemistry B 117(35) (2013) 10304-10310, incorporated herein by reference in its entirety. Moreover, the EO units are thought to improve solubility of the surfactants in high-salinity brine. See J. Lim, E. Kang, H. Lee, B. Lee, Synthesis and interfacial properties of ethoxylated cationic surfactants derived from n-dodecyl glycidyl ether, Journal of Industrial and Engineering Chemistry 22 (2015) 75-82, incorporated herein by reference in its entirety.

In formula (I), $R_1$ and $R_2$ may be the same or different, and each of $R_1$ and $R_2$ are independently selected from the group consisting of a hydrogen, an optionally substituted alkyl, an optionally substituted cycloalkyl, and an optionally substituted arylalkyl. For example, each of $R_1$ and $R_2$ may be independently a hydrogen; an optionally substituted $C_1$ to $C_6$ alkyl, preferably an optionally substituted $C_2$ to $C_5$ alkyl, preferably an optionally substituted $C_3$ to $C_4$ alkyl, preferably an unsubstituted alkyl, for example, methyl, ethyl, or propyl; an optionally substituted cycloalkyl, preferably an optionally substituted $C_3$ to $C_6$ cycloalkyl, preferably an unsubstituted $C_3$ to $C_6$ cycloalkyl such as cyclopropyl, cyclobutyl, cyclopentyl, and cyclohexyl; an optionally substituted aryl, preferably an unsubstituted aryl, preferably phenyl; an optionally substituted $C_7$ to $C_{13}$ arylalkyl, or an optionally substituted $C_8$ to $C_{12}$ arylalkyl, or an optionally substituted $C_9$ to $C_{11}$ arylalkyl, preferably an unsubstituted arylalkyl with benzyl being the most preferable. In some embodiments, each of $R_1$ and $R_2$ are independently a hydrogen, or a methyl. In preferred embodiments, each of $R_1$ and $R_2$ are a hydrogen.

$R_3$ and $R_4$ may be the same or different and may be independently selected from the group consisting of an optionally substituted alkyl, an optionally substituted cycloalkyl, and an optionally substituted arylalkyl. Preferably, $R_3$ and $R_4$ may be independently an optionally substituted $C_1$ to $C_6$ alkyl, an optionally substituted $C_2$ to $C_5$ alkyl, or an optionally substituted $C_3$ to $C_4$ alkyl. Preferably, each of $R_3$ and $R_4$ are independently selected from the group consisting of a methyl, an ethyl, and an isopropyl. the same. In preferred embodiments, each of $R_3$ and $R_4$ are a methyl.

The value of x denotes the number of —$CH_2$— groups connected to the terminal —$CH_3$ group of the surfactant of formula (I), and may range from 2-8, preferably 3-7, preferably 4-6. Most preferably, x is 6.

The value of y denotes the degree of ethoxylation (—O (CH$_2$)$_2$—) and y may range from 1-15, preferably 2-14, preferably 3-13, preferably 4-12, preferably 5-11, preferably 6-10, preferably 7-9. In a preferred embodiment, each of y is an integer in a range of 2-11, 4-9, or 6-8. Most preferably, y is in a range of 6-11, 7-10, or 8-9.

The value of z may be an integer ranging from 4-10, preferably 5-9, preferably 6-8. In preferred embodiments, z is 6.

The value of n denotes the alkyl chain spacer (—C($R_1$) ($R_2$)—) in between the nitrogen atoms (of the amide and the quaternary amine group), and n may be an integer in a range of 2-5, preferably 3-4. Most preferably, n is 3.

The ionic headgroup of the surfactant is represented by A in the structure of formula (I), and in the present disclosure, A is selected from the group consisting of

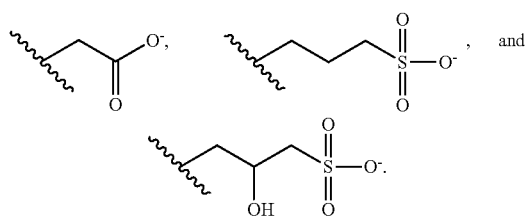

In some embodiments, A is a carboxybetaine group represented by

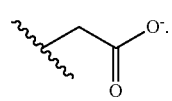

In some embodiments, A is a sulfobetaine group represented by

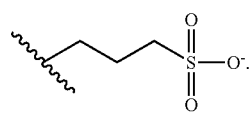

In some embodiments, A is a hydroxy sulfobetaine group represented by

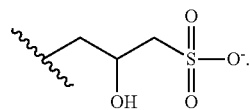

The surfactant herein may be derivable from a mono-unsaturated fatty alcohol (which in turn may be derivable from a mono-unsaturated fatty acid), including both cis-(Z—) unsaturated fatty alcohols such as erucyl alcohol (C22, 13Z), oleyl alcohol (C18, 9Z), palmitoleoyl alcohol (C16, 9Z), myristoleoyl alcohol (C14, 9Z), sapienyl alcohol (C16, 6Z), and the like, as well as trans- (E-) unsaturated fatty alcohols such as elaidyl alcohol (C18, 9E), vaccenyl alcohol (C18, 11E), and the like. In preferred embodiments, the surfactant contains a single site of unsaturation (carbon-carbon double bond), and the single site of unsaturation is in a cis-(Z—) double bond configuration.

In some embodiments, the surfactant has a critical micelle concentration (CMC) in water at 30 to 60° C. of $3\times10^{-5}$ to $5\times10^{-4}$M, preferably $3.3\times10^{-5}$ to $3\times10^{-4}$M, preferably $3.5\times 10^{-5}$ to $1\times10^{-4}$ M, preferably $3.6\times10^{-5}$ to $9\times10^{-5}$ M, preferably $5\times10^{-5}$ to $7\times10^{-5}$ M. In some embodiments, the surfactant has a surface tension at the critical micelle concentration of 31-39 mN/m, preferably 32-38 mN/m, preferably 33-37 mN/m, preferably 34-36 mN/m, preferably 35 mN/m.

The surfactant of the present disclosure typically has a number average molecular weight (Mn) of 415-1,500 g/mol, preferably 450-1,400 g/mol, preferably 500-1,300 g/mol, preferably 600-1,200 g/mol, preferably 700-1,150 g/mol, preferably 750-1,100 g/mol, preferably 800-1,050 g/mol, preferably 850-1,000 g/mol, preferably 900-950 g/mol.

In some embodiments, the surfactant of the present disclosure is soluble in aqueous fluids, even at high temperatures, such as temperatures of up to 150° C., preferably up to 130° C., preferably up to 100° C., preferably up to 90° C., preferably up to 80° C., preferably up to 70° C., preferably up to 60° C., preferably up to 50° C., and remains solubilized at these high temperatures without precipitation or phase separation events for prolonged periods such as up to 100 days, preferably up to 90 days, preferably up to 80 days, preferably up to 70 days, preferably up to 60 days, preferably up to 50 days. The aqueous fluids may include fresh water (e.g., tap water, distilled water, bidi stilled water, deionized water, deionized distilled water, reverse osmosis water, well water, or fresh water obtained from natural sources such as lakes, streams, rivers, etc.) or salt water such as seawater, formation water, produced water, and the like, such as those containing ions of sodium, calcium, magnesium, potassium, sulfate, chloride, bicarbonate, carbonate, and/or bromide, and the like.

In preferred embodiments, the surfactant is selected from the group consisting of

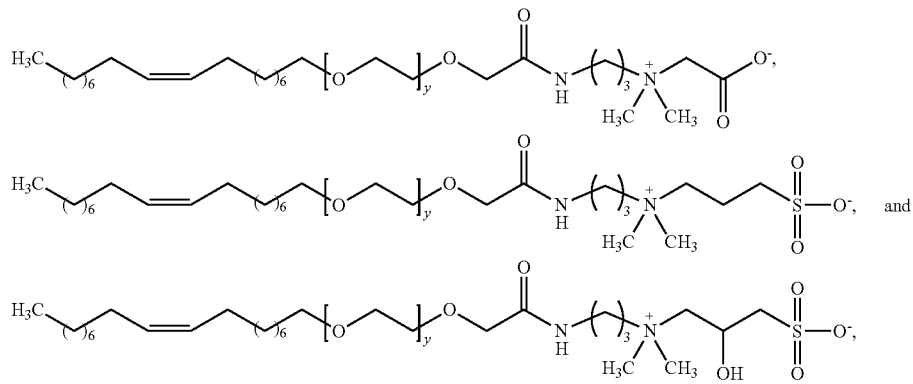

wherein in each structure y is 8 or 9.

Figure 10:
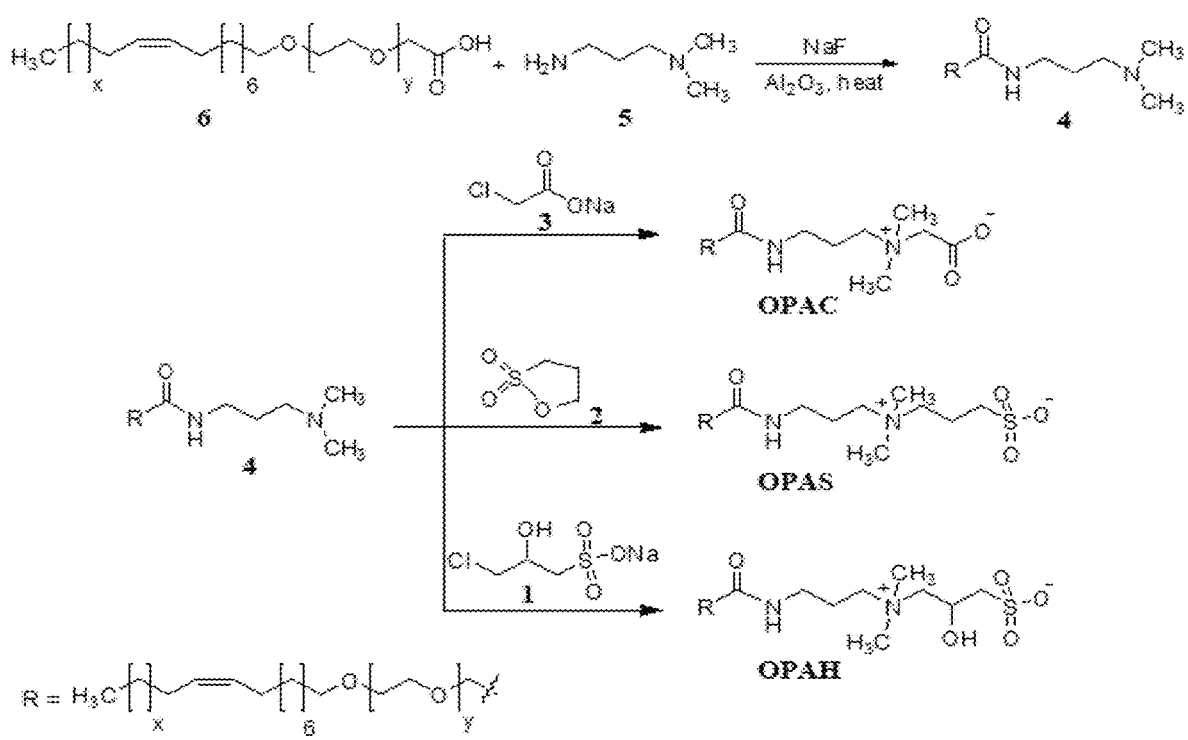
FIG. 10 illustrates the synthesis of betaine type polyoxyethylene zwitterionic surfactants (OPAC, OPAS, and OPAH) containing different ionic headgroups.

The surfactant of formula (I) may be prepared, for example, via the route depicted in FIG. 10. Briefly, a carboxylic acid of formula (II), or a salt thereof, may be obtained, for example, by ethoxylation and subsequent carboxymethylation of a suitable mono-unsaturated fatty alcohol including, but not limited to, myristoleoyl alcohol, palmitoleoyl alcohol, sapienyl alcohol, oleyl alcohol, elaidic acid, vaccenic acid, and erucyl alcohol.

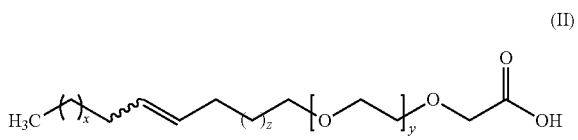

(II)

where x, y, and z are as defined previously.

The carboxylic acid of formula (II) may next be reacted with a diamine of formula (III) to form a tertiary amidoamine intermediate of formula (IV)

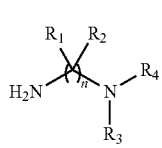

(III)

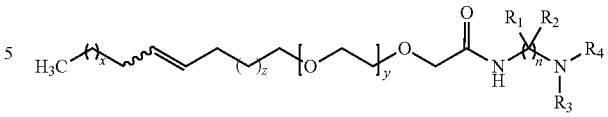

(IV)

where $R_1$, $R_2$, $R_3$, $R_4$, x, y, z, and n are all as defined previously.

Exemplary diamines which fall under the general formula (III) and which may be used in the amidation reaction include, but are not limited to, 3-(dimethylamino)-1-propylamine, 2-(dimethylamino)ethylamine, 2-(diethylamino) ethylamine, 1-dimethylamino-2-propylamine, 3-(diethylamino)-1-propylamine, (3-amino-2-methylpropyl)dimethylamine, (3-amino-1-methylpropyl)dimethylamine, N,N,2,2-tetramethyl-1,3-propanediamine, 4-(dimethylamino) butylamine, 5-(dimethylamino)amylamine, 5-(diethylamino)pentylamine, and 5-(diisopropylamino)amylamine.

The amidation may be performed under a wide variety of amide coupling conditions, including using any amidation reagent/catalyst known to those of ordinary skill in the art to promote/catalyze amide bond formation. In some embodiments, the amidation reaction is performed using a fluoride salt catalyst, including, but not limited to, sodium fluoride, potassium fluoride, silver fluoride, cesium fluoride, and tetrabutylammonium fluoride, preferably sodium fluoride. A molar ratio of the fluoride salt to the carboxylic acid of formula (II) may range from 1:5 to 1:20, preferably 1:6 to 1:18, preferably 1:8 to 1:15, preferably 1:9 to 1:12, or about 1:10. Other amide bond formation reagents and catalysts that may be used in addition to or in lieu of the fluoride salt include, but are not limited to, carbodiimides such as 1-ethyl-3-(3-dimethylaminopropyl)carbodiimide (EDC), N,N-dicyclohexylcarbodiimide (DCC), 1H-benzotriazole derivatives such as 1-[bis(dimethylamino)methylene]-1H-1,2,3-triazolo[4,5-b]pyridinium 3-oxid hexafluorophosphate (HATU), O-(benzotriazol-1-yl)-1,1,3,3-tetramethyluronium hexafluorophosphate (HBTU), O-benzotriazol-1-yl-1,1,3,3-tetramethyluronium tetrafluoroborate (TBTU), as well as phosphoric acid, sulfuric acid, boric acid, silica gel, and zeolites, just to name a few, as well as stoichiometric carboxylic acid activating agents such as oxalyl chloride and thionyl chloride. The amidation may be performed using neat (solvent-free) or solvent-based conditions such as using benzene, xylene, dimethylformamide, tetrahydrofuran, ethyl acetate, diethyl ether, acetonitrile, dimethyl sulfoxide, methylene chloride, chloroform, nitrobenzene, isopropanol, or mixtures thereof. Preferably the amidation is performed under neat conditions. The amidation reaction may be performed using external heat, for example at a temperature of 50-200° C., preferably 100-190° C., preferably 120-180° C., preferably 130-170° C., preferably 150-160° C. using an external heat source, such as an oil bath, an oven, microwave, or a heating mantle. The mixture may be agitated throughout the duration of the reaction by employing a rotary shaker, a magnetic stirrer, or an overhead stirrer, or may be left to stand (i.e. not agitated). Drying agents or other water-removing procedures (e.g., Dean-Stark trap) may optionally be employed to facilitate the removal of water produced as a by-product. Exemplary drying agents include, but are not limited to, aluminosilicate minerals, porous glass, activated carbon, clay, zeolites, anhydrous sodium sulfate, anhydrous magnesium sulfate, anhydrous calcium chloride, and anhydrous calcium sulfate, mesoporous silica, and alumina ($Al_2O_3$), with microporous alumina having an average pore size of 0.2-0.5 nm, or 0.3-0.4 nm being the most preferred.

A molar ratio of the diamine of formula (III) to the carboxylic acid of formula (II) may range from 1:1 to 5:1, preferably 2:1 to 4:1, preferably 3:1 to 3.5:1. In some embodiments, the diamine of formula (III) is introduced into the amidation reaction mixture in single addition or batchwise (e.g., two-stage) fashion. For example, when added batch-wise, 50-70%, 55-65%, or about 57% of a total molar content of the diamine may be added as a first portion and allowed to react with the carboxylic acid for 3-9 hours, 5-7 hours, or about 6 hours, and subsequently 30-50%, 35-45%, or about 43% of a total molar content of the di amine may be added to the same mixture as a second portion and allowed to react with the carboxylic acid for 2-8 hours, 4-6 hours, or about 5 hours, or until the amid coupling reaction is deemed complete. Alternatively, the diamine may be introduced to the reaction mixture in one batch and allowed to react with the carboxylic acid for 5-20 hours, 8-15 hours, or about 12 hours.

The tertiary amido-amine intermediate of formula (IV) may be collected as an oil, washed in acetone, ethyl acetate, and/or isopropanol and then dried, for example, dried under vacuum until a constant weight is achieved.

The tertiary amido-amine intermediate of formula (IV) is then reacted with a suitable electrophile forming the surfactant of formula (I), whereby the tertiary amine is converted into a quaternary ammonium salt attached to a desirable anionic headgroup. In some embodiments, the electrophile is an α-halo acetic acid compound or salt thereof, for example sodium chloroacetate or sodium bromoacetate, to form the surfactant of formula (I) where A is a carboxybetaine group represented by

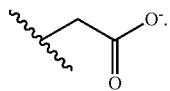

In some embodiments, the electrophile is 1,3-propansultone to form the surfactant of formula (I) where A is a sulfobetaine group represented by

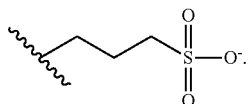

In some embodiments, the electrophile is a 3-halo-2-hydroxypropanesulfonic acid salt (e.g., 3-chloro-2-hydroxypropanesulfonic acid sodium salt) to form the surfactant of formula (I) where A is a hydroxy sulfobetaine group represented by

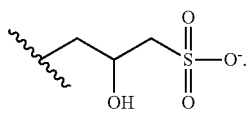

A molar ratio of the electrophile to the tertiary amido-amine intermediate of formula (IV) may range from 1:1 to 2:1, preferably 1.1:1 to 1.8:1, preferably 1.2:1 to 1.7:1, preferably 1.3:1 to 1.6:1, preferably 1.4:1 to 1.5:1. In some embodiments, the tertiary amido-amine intermediate of formula (IV) is reacted with a suitable electrophile in a polar protic solvent such as water, methanol, ethanol, n-propanol, isopropyl alcohol, n-butanol, and mixtures thereof, preferably ethanol:water mixtures. In some embodiments, the tertiary amido-amine intermediate of formula (IV) is reacted with a suitable electrophile in a polar aprotic solvent including, but not limited to, ethyl acetate, dimethylformamide, tetrahydrofuran, acetone, acetonitrile, and dimethyl sulfoxide, preferably ethyl acetate. A base, preferably a carbonate base such as sodium carbonate may also optionally be employed during the surfactant forming step. Reaction between the tertiary amido-amine intermediate of formula (IV) and the electrophile may be thermally promoted using reaction temperatures of up to 120° C., preferably 50-110° C., preferably 60-100° C., preferably 70-95° C., preferably 75-90° C., preferably 80-85° C. Typically, the reaction is performed for 1-48 hours, preferably 5-24 hours, preferably 10-12 hours.

The surfactant may be isolated and purified from the reaction mixture by methods known to those of ordinary skill in the art such as filtration, column chromatography, trituration, and high pressure liquid chromatography (HPLC) (normal phase or reversed phase). Preferred methods include, purifying the reaction mixture with trituration (e.g., using cold acetone) and/or column chromatography (with silica or alumina as the stationary phase). In some embodiments, the surfactant is purified with a silica gel column.

Oil and Gas Well Servicing Fluid

According to a second aspect, the present disclosure relates to an oil and gas well servicing fluid which contains an aqueous base fluid and the surfactant of the present disclosure. The oil and gas servicing fluid is thus intended to be a general fluid that contains the surfactant of the present disclosure for use during various stages of upstream (exploration, field development, and production operations) and midstream (transportation e.g., by pipeline, processing, storage, and distribution) oil recovery operations. For example, the oil and gas well servicing fluid may be used as fracking fluids, drilling fluids, completion fluids, workover fluids, among others, for use for example during drilling, cementing, fracturing, acidizing, demulsification, corrosion inhibition, cleaning, flooding (e.g., waterflooding, chemical flooding, foam and steam flooding), enhanced oil recovery, transportation, and the like.

In preferred embodiments, the oil and gas well servicing fluid is a water-based fluid. The oil and gas well servicing fluid may be formulated using 40-99.999 wt. %, preferably 50-99.9 wt. %, preferably 60-99 wt. %, more preferably 70-95 wt. %, even more preferably 80-90 wt. % of the aqueous base fluid, based on a total weight of the oil and gas well servicing fluid. The aqueous base fluid may be a fresh water (e.g., tap water, distilled water, bidistilled water, deionized water, deionized distilled water, reverse osmosis water, well water, or fresh water obtained from natural sources such as lakes, streams, rivers, etc.) or salt water (e.g., seawater, coastal aquifers, formation water, or wastewater having high salinity).

In particular, the surfactant of the present disclosure offers distinct advantages when employed in harsh oil and gas environments, such as in high salinity environments, and thus the servicing fluid may be formed from formation water (or diluted formation water) or produced water (or diluted produced water). The surfactants are thus suitable for use in servicing fluids with a total dissolved solids content of up to 350,000 ppm (for example when the servicing fluid is made from formation or produced water). In some embodiments, the oil and gas well servicing fluid is formed from a salt water as the aqueous base fluid, preferably sea water, formation water, or produced water and may thus have a total dissolved solids content (TDS) of 50,000-350,000 ppm, preferably 55,000-300,000 ppm, preferably 57,000-250,000 ppm, preferably 58,000-225,000 ppm, preferably 60,000-220,000 ppm, preferably 70,000-215,000 ppm, preferably 80,000-213,000 ppm, preferably 90,000-210,000 ppm, preferably 100,000-200,000 ppm, preferably 120,000-180,000 ppm, preferably 140,000-160,000 ppm.

Representative examples of cations which may be optionally present in the oil and gas well servicing fluid include, but are not limited to, sodium, potassium, magnesium, calcium, strontium, barium, iron (ferrous and ferric), lead, copper, cobalt, manganese, nickel, zinc, aluminum, chromium, and titanium, as well as mixtures thereof. Representative examples of anions which may be present in the oil and gas well servicing fluid include, but are not limited to, chloride, carbonate, bicarbonate, sulfate, bromide, iodide, acetate, hydroxide, sulfide, hydrosulfide, chlorate, fluoride, hypochlorite, nitrate, nitrite, perchlorate, peroxide, phosphate, phosphite, sulfite, hydrogen phosphate, hydrogen sulfate, as well as mixtures thereof.

While the amounts of individual ions present may vary significantly based on the location of the well, the water source used to formulate the servicing fluid, whether or not the water source is diluted, etc., the oil and gas well servicing fluid may generally contain up to 320,000 ppm total of monovalent ions, for example at least 300 ppm, preferably at least 400 ppm, preferably at least 500 ppm, preferably at least 1,000 ppm, preferably at least 2,000 ppm, preferably at least 5,000 ppm, preferably at least 10,000 ppm, preferably at least 15,000 ppm, preferably at least 20,000 ppm, preferably at least 50,000 ppm, preferably at least 100,000 ppm, preferably at least 125,000 ppm, preferably at least 150,000 ppm, preferably at least 175,000 ppm, preferably at least 190,000, and up to 320,000 ppm, preferably up to 300,000 ppm, preferably up to 275,000 ppm, preferably up to 250,000 ppm, preferably up to 225,000 ppm, preferably up to 200,000 ppm total of monovalent ions. In some embodiments, chloride ions may be present in the oil and gas well servicing fluid in amounts of at least 100 ppm, preferably at least 1,000 ppm, preferably at least 5,000 ppm, preferably at least 10,000 ppm, preferably at least 20,000 ppm, preferably at least 25,000 ppm, and up to 250,000 ppm, preferably up to 200,000 ppm, preferably up to 175,000 ppm, preferably up to 150,000 ppm, preferably up to 135,000 ppm, preferably up to 100,000 ppm, preferably up to 50,000 ppm, preferably up to 35,000 ppm. In some embodiments, sodium ions may be present in the oil and gas well servicing fluid in amounts of at least 50 ppm, preferably at least 100 ppm, preferably at least 1,000 ppm, preferably at least 5,000 ppm, preferably at least 10,000 ppm, preferably at least 15,000 ppm, and up to 60,000 ppm, preferably up to 55,000 ppm, preferably up to 45,000 ppm, preferably up to 30,000 ppm, preferably up to 25,000 ppm, preferably up to 20,000 ppm.

The amount of the surfactant of formula (I) present in the oil and gas well servicing fluid may be varied depending on the drilling operation, wellbore conditions, and the nature of other components in the oil and gas well servicing fluid. However, typically, the surfactant disclosed herein is employed in an amount of 0.001-15 wt. %, preferably 0.005-14 wt. %, preferably 0.01-13 wt. %, preferably 0.015-12 wt. %, preferably 0.02-11 wt. %, preferably 0.025-10 wt. %, preferably 0.03-8 wt. %, preferably 0.035-6 wt. %, preferably 0.04-4 wt. %, preferably 0.045-2 wt. %, preferably 0.05-1 wt. %, preferably 0.055-0.5 wt. %, preferably 0.06-0.1 wt. % relative to a total weight of the oil and gas well servicing fluid.

The oil and gas well servicing fluid may optionally contain an oil/oil phase, for example, the oil and gas well servicing fluid may contain up to 20 wt. % of an oil phase, preferably 0.05-15 wt. %, preferably 0.5-10 wt. %, preferably 1-9 wt. %, preferably 1.5-8 wt. %, preferably 2-7 wt. %, preferably 2.5-6 wt. %, preferably 3-5 wt. %, preferably 3.5-4 wt. %, of an oil/oil phase, based on a total weight of the oil and gas well servicing fluid. In some embodiments, the oil is obtained from a subterranean reservoir and the oil is crude oil. The crude oil may be a very light crude oil such as Arab Extra Light, Arab Super Light, or Arab Super Light Ardjuna crude oil (e.g., a jet fuel, gasoline, kerosene, petroleum ether, petroleum spirit, or petroleum naphtha crude oil), a light crude oil such as Arab Light or Arab Light/Seg 17 Blend crude oil (e.g., grade 1 and grade 2 fuel oil, diesel fuel oil, domestic fuel oil), a medium crude oil such as Arab Medium crude oil, and a heavy crude oil such as Arab Heavy crude oil (e.g., grade 3, 4, 5, and 6 fuel oil, heavy marine fuel), including both sweet (sulfur volume lower than 0.50%) and sour (sulfur volume higher than 0.50%) crude oils varieties. Of course, the oil/oil phase is not limited to crude petroleum oil, but extends to any hydrocarbon which may be added during oil recovery operations, such as kerosene, gasoline, diesel oils, gas oils, fuel oils, paraffin oils, mineral oils (e.g., refined mineral oil, low toxicity mineral oils), other petroleum distillates, synthetic oils (e.g., polyolefins, polydiorganosiloxanes, siloxanes, organosiloxanes), as well as mixtures thereof.

In some embodiments, the oil and gas well servicing fluid has a pH of at least 1, preferably at least 2, preferably at least 3, preferably at least 4, preferably at least 5, preferably at least 6, preferably at least 7, and up to 14, preferably up to 13, preferably up to 12, preferably up to 11, preferably up to 10, preferably up to 9, preferably up to 8.

In addition to being compatible with the various salts and ionic species provided above, even in water sources having an extremely high TDS content, the surfactant of the present disclosure is also compatible with a wide range of components, species, chemistries, materials, additives common to oil and/or gas production. For example, the oil and gas well servicing fluid may be used as a fracking fluid, a drilling fluid, a completion fluid, and/or a workover fluid, and may additionally comprise one or more of oil (e.g., produced petroleum), natural gas, carbon dioxide, hydrogen sulfide, organosulfur (e.g., a mercaptan), hydronium ions, oxygen, etc., as well as one or more of other chemistries/materials/additives known to those of ordinary skill in the art used to effect production or fluid properties during oil recovery operations. Such other chemistries/materials/additives may be used during various oil and gas well operations in art acceptable quantities. For example, secondary surfactants may be optionally included in the oil and gas well servicing fluids herein, including cationic, anionic, non-ionic, and/or amphoteric secondary surfactants.

Cationic surfactants may include, but are not limited to
a protonated amine formed from a reaction between a $C_6$-$C_{26}$ alkyl amine compound and an acid (e.g., acetic acid, formic acid, propionic acid, butyric acid, pentanoic acid, hexanoic acid, oxalic acid, malonic acid, lactic acid, glyceric acid, glycolic acid, malic acid, citric acid, benzoic acid, p-toluenesulfonic acid, trifluoromethanesulfonic acid, hydrochloric acid, nitric acid, phosphoric acid, sulfuric acid, hydrobromic acid, perchloric acid, hydroiodic acid, etc.), such as protonated salts of $C_6$-$C_{26}$ alkyl monoamines, $C_6$-$C_{26}$ alkyl (poly)alkylene polyamines, and alkoxylated fatty amines;

a protonated $C_6$-$C_{26}$ alkyl amidoamine formed from a reaction between a $C_6$-$C_{26}$ alkyl amidoamine compound and an acid (for example the acids listed above), such as protonated forms of the amide reaction product between any fatty acid previously listed (or ester derivative thereof) with a polyamine (e.g., putrescine, cadaverine, ethylene diamine, $N^1,N^1$-dimethylethane-1,2-diamine, $N^1,N^1$-dimethylpropane-1,3-diamine, $N^1,N^1$-diethylethane-1,2-diamine, $N^1,N^1$-diethylpropane-1,3-diamine, spermidine, 1,1,1-tris(aminomethyl)ethane, tris(2-aminoethyl)amine, spermine, TEPA, DETA, TETA, AEEA, PEHA, HEHA, dipropylene triamine, tripropylene tetramine, tetrapropylene pentamine, pentapropylene hexamine, hexapropylene heptamine, dibutylene triamine, tributylene tetramine, tetrabutylene pentamine, pentabutylene hexamine, hexabutylene heptamine), with specific mention being made to protonated forms of stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, and arachidamidoethyldimethylamine; and a quaternary ammonium compound made from alkylation with suitable alkylating agents (e.g., dimethyl sulfate, methyl chloride or bromide, benzyl chloride or bromide, $C_6$-$C_{26}$ alkyl chloride or bromide, etc.) of a tertiary $C_6$-$C_{26}$ alkyl amine, an alkoxylated (tertiary) amine, or an aprotic nitrogenous heteroarene (optionally substituted) having at least one aromatic nitrogen atom with a reactive lone pair of electrons, with specific mention being made to a tri-fatty alkyl lower alkyl ammonium compound (e.g., trioctyl methyl ammonium chloride), a $C_{10}$-$C_{18}$ alkyl trimethyl ammonium chloride or methosulfate, a di-$C_{10}$-$C_{18}$ alkyl dimethyl ammonium chloride or methesulfate, a $C_{10}$-$C_{18}$ alkyl benzyl dimethyl ammonium chloride, a methyl quaternized $C_6$-$C_{22}$ alkyl propylene diamine, a methyl quaternized $C_6$-$C_{22}$ alkyl propylene triamine, a methyl quaternized $C_6$-$C_{22}$ alkyl propylene tetraamine, a N—$C_{10}$-$C_{18}$alkyl pyridinium or a quinolinium bromide or chloride such as N-octyl pyridinium bromide, N-nonyl pyridinium bromide, N-decyl pyridinium bromide, N-dodecyl pyridinium bromide, N-tetradecyl pyridinium bromide, N-dodecyl pyridinium chloride, N-cyclohexyl pyridinium bromide, naphthyl methyl quinolinium chloride, naphthyl methyl pyridinium chloride, and cetylpyridinium chloride (for example those disclosed in CN101544903B—incorporated herein by reference in its entirety);

as well as mixtures thereof.

Anionic surfactants may include, but are not limited to:
sulfates, such as alkyl sulfates, alkyl-ester-sulfates, alkyl ether sulfates, alkyl-alkoxy-ester-sulfate, sulfated alkanolamides, glyceride sulfates, in particular, sulfates of fatty alcohols or polyoxyalkylene ethers of fatty alcohols such as sodium dodecyl sulfate, sodium laureth sulfate, ammonium lauryl sulfate, potassium lauryl sulfate, sodium myreth sulfate;

sulfonates such as alkyl sulfonates, fatty alkyl-benzene sulfonates, lower alkyl-benzene sulfonates, alpha olefin sulfonates, lignosulfonates, sulfo-carboxylic compounds, for example, dodecyl benzene sulfonate, dioctyl sodium sulfosuccinate, perfluorooctanesulfonate (PFOS), perfluorobutanesulfonate;

phosphates such as alkyl aryl ether phosphates, alkyl ether phosphates, phosphates of fatty alcohols or polyoxyalkylene ethers of fatty alcohols such as cetyl phosphate salts, dicetyl phosphate salts, ceteth-10-phosphate salts;

carboxylate salts of fatty acids, acylamino acids, lactylates, and/or fatty alcohols/polyoxyalkylene ethers of fatty alcohols such as sodium stearate, vegetable oil-based anionic surfactants (e.g., palm oil anionic surfactant), sodium behenoyl lactylate, sodium isostearoyl lactylate, sodium caproyl lactylate, sodium laureth-5 carboxylate, sodium laureth-6 carboxylate, sodium laureth-11 carboxylate, and mixtures thereof.

Non-ionic surfactants may include, but are not limited to:
amides or alkanolamides of fatty acids, that is, amide reaction products between a fatty acid and an amine or alkanolamine compound, such as coconut fatty acid monoethanolamide (e.g., N-methyl coco fatty ethanol amide), coconut fatty acid diethanolamide, oleic acid diethanolamide, palm based oleylamine, and vegetable oil fatty acid diethanolamide;

alkoxylated alkanolamides of fatty acids, preferably ethoxylated and/or propoxylated variants of the alkanolamides of fatty acids using for example anywhere from 2 to 30 EO and/or PO molar equivalents, preferably 3 to 15 EU and/or PU molar equivalents, preferably 4 to 10 EU and/or PU molar equivalents, preferably 5 to 8 EU and/or PU molar equivalents per moles of the alkanolamide of the fatty acid (e.g., coconut fatty acid monoethanolamide with 4 moles of ethylene oxide);

amine oxides, such as N-cocoamidopropyl dimethyl amine oxide and dimethyl $C_6$-$C_{22}$ alkyl amine oxide (e.g., dimethyl coco amine oxide);

fatty esters, such as ethoxylated and/or propoxylated fatty acids (e.g., castor oil with 2 to 40 moles of ethylene oxide), alkoxylated glycerides (e.g., PEG-24 glyceryl monostearate), glycol esters and derivatives, monoglycerides, polyglyceryl esters, esters of polyalcohols, and sorbitan/sorbitol esters;

ethers, such as (i) alkoxylated $C_1$-$C_{22}$ alkanols, which may include alkoxylated $C_1$-$C_5$ alkanols, preferably ethoxylated or propoxylated $C_1$-$C_5$ alkanols (e.g., dipropylene glycol n-butyl ether, tripropylene glycol n-butyl ether, dipropylene glycol methyl ether, tripropylene glycol methyl ether, diethylene glycol n-butyl ether, triethylene glycol n-butyl ether, diethylene glycol methyl ether, triethylene glycol methyl ether) and alkoxylated $C_6$-$C_{26}$ alkanols (including alkoxylated fatty alcohols), preferably alkoxylated $C_7$-$C_{22}$ alkanols, more preferably alkoxylated $C_8$-$C_{14}$ alkanols, preferably ethoxylated or propoxylated (e.g., cetyl stearyl alcohol with 2 to 40 moles of ethylene oxide, lauric alcohol with 2 to 40 moles of ethylene oxide, oleic alcohol with 2 to 40 moles of ethylene oxide, ethoxylated lanoline derivatives, laureth-3, ceteareth-6, ceteareth-11, ceteareth-15, ceteareth-16, ceteareth-17, ceteareth-18, ceteareth-20, ceteareth-23, ceteareth-25, ceteareth-27, ceteareth-28, ceteareth-30, isoceteth-20, laureth-9/myreth-9, and PPG-3 caprylyl ether); (ii) alkoxylated polysiloxanes; (iii) ethylene oxide/propylene oxide copolymers (e.g., PPG-1-PEG-9-lauryl glycol ether, PPG-12-buteth-16, PPG-3-buteth-5, PPG-5-buteth-7, PPG-7-buteth-10, PPG-9-buteth-12, PPG-12-buteth-16, PPG-15-buteth-20, PPG-20-buteth-30, PPG-28-buteth-35, and PPG-33-buteth-45); and (iv) alkoxylated alkylphenol s;

alkyl polyglycosides (APGs) such as those made from reaction between fatty alcohols and glucose;

and mixtures thereof.

Amphoteric surfactants may include, but are not limited to:

$C_6$-$C_{22}$ alkyl dialkyl betaines, such as fatty dimethyl betaines (R—N(CH$_3$)$_2$($^+$)—CH$_2$COO$^-$), obtained from a $C_6$-$C_{22}$ alkyl dimethyl amine which is reacted with a monohaloacetate salt (e.g., sodium monochloroacetate), such as $C_{12}$-$C_{14}$ dimethyl betaine (carboxylate methyl $C_{12}$-$C_{14}$ alkyl dimethylammonium);

$C_6$-$C_{22}$ alkyl amido betaines (R—CO—NH—CH$_2$CH$_2$CH$_2$—N(CH$_3$)$_2$($^+$)—CH$_2$COO$^-$ or R—CO—NH—CH$_2$CH$_2$—N(CH$_3$)$_2$($^+$)—CH$_2$COO$^-$), obtained by the reaction of a monohaloacetate salt (e.g., sodium monochloroacetate) with the reaction product of either dimethyl amino propylamine or dimethyl amino ethylamine with a suitable carboxylic acid or ester derivatives thereof, such as $C_{10}$-$C_{18}$ amidopropyl dimethylamino betaine;

$C_6$-$C_{22}$ alkyl sultaines or $C_6$-$C_{22}$ alkyl amido sultaines, which are similar to those $C_6$-$C_{22}$ alkyl dialkyl betaines or $C_6$-$C_{22}$ alkyl amido betaines described above except in which the carboxylic group has been substituted by a sulfonic group (R—N(CH$_3$)$_2$O—CH$_2$CH$_2$CH$_2$SO$_3^-$ or R—CO—NH—CH$_2$CH$_2$CH$_2$—N(CH$_3$)$_2$($^+$) CH$_2$CH$_2$CH$_2$SO$_3^-$ or R—CO—NH—CH$_2$CH$_2$—N(CH$_3$)$_2$($^+$)—CH$_2$CH$_2$CH$_2$SO$_3^-$) or a hydroxysulfonic group (R—N(CH$_3$)$_2$($^+$)—CH$_2$CH(OH)—CH$_2$SO$_3^-$ or R—CO—NH—CH$_2$CH$_2$CH$_2$—N(CH$_3$)$_2$($^+$)—CH$_2$CH (OH)—CH$_2$SO$_3^-$ or R—CO—NH—CH$_2$CH$_2$—N (CH$_3$)$_2$($^+$)—CH$_2$CH(OH)—CH$_2$SO$_3^-$), such as $C_{10}$-$C_{18}$ dimethyl hydroxysultaine and $C_{10}$-$C_{18}$ amido propyl dimethylamino hydroxysultaine;

and mixtures thereof.

In some embodiments, the only surfactant present in the oil and gas well servicing fluids herein are surfactants represented by formula (I).

Other chemistries/materials/additives which may be optionally included in the oil and gas well servicing fluid in art appropriate levels, include, but are not limited to, pH regulating agents e.g., $H_2SO_4$, HCl, NaOH, phosphate buffers such as monosodium phosphate, disodium phosphate, sodium tripolyphosphate buffers, borate buffers;

viscosity modifying agents e.g., bauxite, bentonite, dolomite, limestone, calcite, vaterite, aragonite, magnesite, taconite, gypsum, quartz, marble, hematite, limonite, magnetite, andesite, garnet, basalt, dacite, nesosilicates or orthosilicates, sorosilicates, cyclosilicates, inosilicates, phyllosilicates, tectosilicates, kaolins, montmorillonite, fullers earth, and halloysite xanthan gum, psyllium husk powder, hydroxyethyl cellulose, carboxymethylcellulose, and polyanionic cellulose, poly (diallyl amine), diallyl ketone, diallyl amine, styryl sulfonate, vinyl lactam, laponite;

chelating agents e.g., ethylene diamine tetraacetic acid (EDTA), diethylene triamine pentaacetic acid (DPTA), hydroxyethylene diamine triacetic acid (HEDTA), ethylene diamine di-ortho-hydroxy-phenyl acetic acid (EDDHA), ethylene diamine di-ortho-hydroxy-para-methyl phenyl acetic acid (EDDHMA), ethylene diamine di-ortho-hydroxy-para-carboxy-phenyl acetic acid (EDDCHA);

stabilizing agents e.g., ethylene glycol, propylene glycol, glycerol, polypropylene glycol, polyethylene glycol, carboxymethyl cellulose, hydroxyethyl cellulose, xanthan gums, polyacrylamides, polysiloxane polyalkyl polyether copolymers, acrylic copolymers, alkali metal alginates and other water soluble alginates, carboxyvinyl polymers, polyvinylpyrollidones, polyacrylates;

intensifiers e.g., formic acid, $C_1$-$C_4$ alkyl formates such as methyl formate and ethyl formate, benzyl formate, formamide, dimethyl formamide, 1,1'-azobisformamide, metal halides such as sodium bromide, potassium bromide, sodium iodide, potassium iodide, copper(I) chloride, copper(I) iodide, copper(II) chloride, copper (II) iodide, antimony chloride, preferably CuI, KI, and formic acid, more preferably CuI;

corrosion inhibitors e.g., polyureas, alkoxylated fatty amines, chromates, zinc salts, (poly)phosphates, organic phosphorus compounds (phosphonates), acetylenic alcohols such as propargylic alcohol, α,β-unsaturated aldehydes such as cinnameldehyde and crotonaldehyde, aromatic aldehydes such as furfural, p-anisaldehyde, phenones including alkenyl phenones such as phenyl vinyl ketone, nitrogen-containing heterocycles such as imidazolines, piperazines, hexamethylene tetramines, quaternized heteroarenes such as 1-(benzyl) quinolinium chloride, and condensation products of carbonyls and amines such as Schiff bases;

dispersing agents e.g., polymeric or co-polymeric compounds of polyacrylic acid, polyacrylic acid/maleic acid copolymers, styrene/maleic anhydride copolymers, polymethacrylic acid and polyaspartic acid;

scale inhibitors e.g., sodium hexametaphosphate, sodium tripolyphosphate, hydroxyethylidene diphosphonic acid, aminotris(methylenephosphonic acid (ATMP), vinyl sulfonic acid, allyl sulfonic acid, polycarboxylic acid polymers such as polymers containing 3-allyloxy- 2-hydroxy-propionic acid monomers, sulfonated polymers such as vinyl monomers having a sulfonic acid group, polyacrylates;

defoaming agents e.g., silicone oils, silicone oil emulsions, organic defoamers, emulsions of organic defoamers, silicone-organic emulsions, silicone-glycol compounds, silicone/silica adducts, emulsions of silicone/silica adducts;

proppants e.g., sand, ceramic, silica, quartz, or other particulates that prevent fractures from closing when injection is stopped;

emulsifiers such as a tallow amine, a ditallow amine, or combinations thereof, for example a 50% concentration of a mixture of tallow alkyl amine acetates, C16-C18 (CAS 61790-60) and ditallow alkyl amine acetates (CAS 71011-03-5) in a suitable solvent such as heavy aromatic naphtha and ethylene glycol;

clay swelling inhibitors e.g., potassium chloride, potassium bromide, potassium formate, potassium fluoride, and potassium iodide;

winterizers e.g., methanol;

as well as other oil/gas production additives such as hydrate inhibitors, asphaltene inhibitors, paraffin inhibitors, $H_2S$ scavengers, $O_2$ scavengers, $CO_2$ scavengers, friction reducing agents, water clarifiers, breakers, biocides, crosslinkers, among many others;

as well as mixtures thereof.

Methods of Servicing an Oil and Gas Well

A third aspect of the present disclosure relates to a method of servicing an oil and gas well during fracking, drilling, completion, and/or workover using the oil and gas well servicing fluid. The method herein is not limited to any particular type of well, as vertical, horizontal, multilateral, and extended reach wells may be serviced with the disclosed oil and gas well servicing fluid. The surfactant is compatible with, and thus may be added to, any subterranean geological formation including a shale formation, a clay formation, a carbonate formation, a sandstone formation, or the like. In some embodiments, the subterranean geological formation is a shale formation, which contains clay minerals and quartz. In some embodiments, the subterranean geological formation is a clay formation, which contains chlorite, illite, kaolinite, montmorillonite and smectite. In some embodiments, the subterranean geological formation is a carbonate formation, e.g. limestone or dolostone, which contains carbonate minerals, such as calcite, aragonite, dolomite, etc., or a sandstone formation, for example, a formation which contains quartz, feldspar, rock fragments, mica and numerous additional mineral grains held together with silica and/or cement.

A pumping system may be used to circulate the oil and gas well servicing fluid in a wellbore during the desired servicing operation. Use of the oil and gas well servicing fluid for a particular operation also does not preclude the use of other servicing operations. For example, the oil and gas well servicing fluid may be used as a drilling fluid and other operations may still be used in conjunction with or sequential to, the drilling operation, such as pre-flush treatments, after-flush treatments, hydraulic fracturing treatments, sand control treatments (e.g., gravel packing), "frac pack" treatments, matrix acidizing, wellbore clean-out treatments, cementing operations, workover treatments, etc.

The servicing fluid may be directly injected into a pipe in fluid communication with the subterranean reservoir, optionally under pressure, or alternatively the surfactant of formula (I) may be directly injected into the subterranean reservoir where it is combined with an aqueous base fluid (e.g., formation water) thereby forming the servicing fluid. In any of the above applications, the surfactant/servicing fluid may be injected continuously and/or in batches. In some embodiments, the oil and gas servicing fluid is used for fracking operations and is injected into the well at pressures above the fracture point of the formation, for example pressures of up to 15,000 psi, preferably up to 13,000 psi, preferably up to 10,000 psi, preferably up to 9,000 psi, preferably up to 8,000 psi, preferably up to 7,000 psi, preferably up to 6,000 psi, preferably up to 5,000 psi. In some embodiments, the oil and gas well servicing fluid is injected at pressures less than the fracture pressure of the formation, for example at pressures of up to 4,000 psi, preferably up to 3,000 psi, preferably up to 2,000 psi, preferably up to 1,000 psi, preferably up to 800 psi, preferably up to 600 psi, preferably up to 400 psi, preferably up to 200 psi, preferably up to 100 psi, preferably up to 80 psi, preferably up to 60 psi, preferably up to 40 psi, preferably up to 35 psi, preferably up to 30 psi, preferably up to 25 psi, preferably up to 20 psi.

The servicing fluid may be injected using addition/dosing/mixing techniques known by those of ordinary skill in the art, including both manual and automatic addition techniques. For example, the addition may be carried out by using inline static mixers, inline mixers with velocity gradient control, inline mechanical mixers with variable speed impellers, inline jet mixers, motorized mixers, batch equipment, and appropriate chemical injection pumps and/or metering systems. The chemical injection pump(s) can be automatically or manually controlled to inject any amount of the surfactant/servicing fluid.

The surfactants described herein are effective under a variety of conditions, even under harsh conditions which may be encountered during challenging oil/gas recovery operations (high temperature and/or high salinity environments). In some embodiments, the surfactants prevent precipitation and/or phase separation events at temperatures of 30-150° C., preferably 40-140° C., preferably 50-130° C., preferably 60-120° C., preferably 70-110° C., preferably 80-100° C., preferably 90-95° C. In particular, the surfactants remain effective at these high temperatures even in high salinity environments, such as those with the total dissolved solids contents described previously, for prolonged periods of time, e.g., up to 100 days, preferably up to 90 days, preferably up to 80 days, preferably up to 70 days, preferably up to 60 days, preferably up to 50 days.

The examples below are intended to further illustrate protocols for preparing/characterizing the surfactants of formula (I), and uses thereof, and are not intended to limit the scope of the claims.

EXAMPLES

Experimental

Material

Glycolic acid ethoxylate oleyl ether, 3-(dimethylamino)-1-propylamine (99%), 1,3-propanesultone (98%), 3-chloro-2-hydroxypropanesulfonic acid sodium salt (95%), sodium chloroacetate (98%), sodium fluoride (≥99%), Aluminum oxide (≥98% $Al_2O_3$ basis) were purchased from Aldrich company Solvents were purified through distillation for the preparation of OPAC, OPAS, and OPAH. Salts were purchased from Aldrich company for the preparation of seawater (SW) and formation water (FW), including sodium bicarbonate ($NaHCO_3$), sodium chloride (NaCl), calcium chloride (CaCl$_2$), sodium sulfate (Na$_2$SO$_4$), and magnesium sulfate (MgSO$_4$) The amount of each salt in SW and FW is depicted in Table 1.

TABLE 1

The composition of seawater and formation water

| Ions | FW (g L$^{-1}$) | SW (g L$^{-1}$) |
| --- | --- | --- |
| Na$^+$ | 59.5 | 18.3 |
| Ca$^{2+}$ | 19.1 | 0.7 |
| Mg$^{2+}$ | 2.5 | 2.1 |
| So$_4^{2-}$ | 0.4 | 4.3 |
| Cl$^-$ | 132.1 | 32.2 |
| HCO$_3^-$ | 0.4 | 0.1 |
| Total | 214 | 57.7 |

Structure Elucidation

NMR (Nuclear Magnetic Resonance) study was done with the help of JEOL 1500 machine (500 MHz). TMS was used as an internal standard, samples were dissolved in chloroform-d, and readings were recorded in ppm. FTIR analysis was conducted with the help of Perkin-Elmer instrument (16F model) and readings were noted in cm$^{-1}$.

Thermogravimetric Analysis (TGA)

TGA graph was obtained using SDT Q600 machine (TA instrument) with continuous heating at 20° C./min. The heating range 30-500° C. with a stable flow of nitrogen at 100 mL/min.

Salt Tolerance 10 wt % solutions of OPAC, OPAS, and OPAH were prepared in DW, SW, and FW and kept in the oven for 90 days at 90° C. A transparent solution after 90 days revealed that OPAC, OPAS, and OPAH are compatible and soluble with all kinds of water. Less soluble material exhibit phase separation and/or precipitation when dissolved in water.

Surface Tension

Surface activities of OPAC, OPAS, and OPAH were determined using a force tensiometer with a platinum Wilhelmy plate (Sigma 702, Biolin Scientific). The test temperatures were 30° C. and 60° C. The plate was flushed with deionized water before heating it red hot to ensure it was properly cleaned. The surface tension of deionized water was measured three times to check if the cleanup procedure yielded repeatable results. The samples were covered to minimize evaporation, but with enough space to let the plate go through the covering during the measurement.

The surface tension data was used to estimate other properties using the following equations:

$$\pi_{cmc} = \gamma_0 - \gamma_{cmc} \quad (1)$$

$$\Gamma_{max} = -\frac{1}{nRT}\left(\frac{d\gamma}{d\ln C}\right)_T \quad (2)$$

$$A_{min} = 10^{18}/N_A\Gamma_{max} \quad (3)$$

where cmc is critical micelle concentration, $\gamma_0$ represents surface tension of water without surfactant, $\gamma_{cmc}$ is surface tension at cmc, $\pi_{cmc}$ Represents the ability of the surfactant to reduce the surface tension, $\Gamma_{max}$ is the maximum surface access, Avogadro number is represented by $N_A$, $d\gamma/d\ln C$ is the slope, C represents the concentration of surfactant, temperature, and gas constant are represented by T and R, respectively, $A_{min}$ is the minimum area per molecule, and the values of n is 1 for zwitterionic surfactants.

Synthesis

Synthesis of Tertiary Amido-Amine Intermediate (4)

The intermediate compound (4) was synthesized by following the method outlined in FIG. 10. See Z. Chu, Y. Feng, A facile route towards the preparation of ultra-long-chain amidosulfobetaine surfactants, Synlett 2009(16) (2009) 2655-2658, incorporated herein by reference in its entirety. 3-(dimethylamino)-1-propylamine (5) (2.92 g, 85.71 mmol), glycolic acid ethoxylate oleyl ether (6) (30 g, 42.86 mmol), NaF (0.18 g, 4.29 mmol) were refluxed in 200 mL 3-necked RB flask for 6 hours at 160° C. The resulting water as a byproduct was collected with the help of Al$_2$O$_3$. The reaction continued for 6 h and then additional 3-(dimethylamino)-1-propylamine (6.57 g, 64.29 mmol) was injected in the reaction flask and reaction continued for further 5 hours. After completion of the reaction, the residual 3-(dimethylamino)-1-propylamine was separated, and the crude product was dissolved in acetone, filtered, and vacuumed to attain tertiary amido-amine (4), which is a yellowish viscous material. $^1$H-NMR (500 MHz, CDCl$_3$, TMS) δ ppm: 0.87 (t, J=6.7 Hz, CH$_3$), 1.14-1.34 (m, (CH$_2$)$_n$), 1.51-1.61 (m, CH$_2$), 1.70 (t, J=7.0 Hz, CH$_2$), 2.03 (m, (CH$_2$)$_2$), 2.24 (s, (2×CH$_3$), 2.36 (t, J=7.0 Hz, CH$_2$), 3.30-3.40 (m, CH$_2$), 3.45 (t, J=7.0 Hz, CH$_2$), 3.55-3.60 (m, CH$_2$), 3.61-3.71 (m, (OCH$_2$CH$_2$)$_n$), 4.00 (s, CH$_2$), 5.34 (m, CH═CH), 7.54 (s, NH).

Synthesis of Oleyl Polyoxyethylene Amindopropyl Carboxybetaine (OPAC)

The intermediate 4 (10.0 g, 12.76 mmol) and sodium chloroacetate (3) (1.86 g, 15.94 mmol) were dissolved in ethanol:water (75:15 mL) using round bottom flask (3-necked, 500 Ml). The experiment was continued at 85° C. for 12 hours. The pale yellow viscous material was obtained, filtered, washed with ethyl acetate (3×50 mL). The viscous product was further purified using column chromatography. The column was filled with silica and ethanol was used as a mobile phase to achieve the required surfactant OPAC (See Y. Zhang, Y. Luo, Y. Wang, J. Zhang, Y. Feng, Single-component wormlike micellar system formed by a carboxylbetaine surfactant with C22 saturated tail, Colloids and Surfaces A: Physicochemical and Engineering Aspects 436 (2013) 71-79, incorporated herein by reference in its entirety), which was obtained as a colorless gel. $^1$H-NMR (500 MHz, CDCl$_3$, TMS) δ ppm: 0.88 (t, CH$_3$, J=6.7 Hz), 1.16-1.36 (m, (CH$_2$)$_n$), 1.53-1.63 (m, CH$_2$), 1.95-2.05 (m, (CH$_2$)$_2$), 3.24 (s, 2×CH$_3$), 3.31-3.41 (m, CH$_2$), 3.41-3.51 (m, CH$_2$), 3.52-3.72 (m, (OCH$_2$CH$_2$)—), 4.00 (m, CH$_2$), 5.34 (m, CH═CH), 8.00 (s, NH). $^{13}$C-NMR δ (ppm): 14.1, 22.7, 24.8, 26.1, 27.2, 29.2, 29.3, 29.4, 29.5, 29.6, 29.7, 29.8, 31.9, 35.9, 42.8, 51.5, 55.3, 61.6, 64.4, 69.1-72.7, 129.8, 129.9, 165.0, 170.8. FT-IR υ (cm$^{-1}$) 3398, 2923, 2855, 1634, 1460, 1394, 1348, 1250, 1095, 946.

Synthesis of Oleyl Polyoxyethylene Amidopropyl Sulfobetaine (OPAS)

The intermediate 4 (10.0 g, 12.76 mmol) and 1,3-propanesultone (2) (2.34 g, 19.13 mmol) were dissolved in ethyl acetate (100 mL) using a round bottom flask (3-necked, 500 mL). The experiment was continued at 80° C. for 12 hours. The pale yellow viscous gel was received, dissolved in cold acetone (3×50 mL), filtered, and vacuumed to obtain OPAS (See Z. Chu, Y. Feng, A facile route towards the preparation of ultra-long-chain amidosulfobetaine surfactants, Synlett 2009 (16) (2009) 2655-2658, incorporated herein by reference in its entirety) as a colorless viscous material. $^1$H-NMR (500 MHz CDCl$_3$, TMS) δ ppm: 0.88 (t, CH$_3$, J=6.7 Hz), 1.17-1.37 (m, (CH$_2$)$_n$), 1.53-1.63 (m, CH$_2$), 1.95-2.05 (m, ($CH_2$)$_3$), 2.16-2.26 (m, $CH_2$), 2.85-2.95 (m, ($CH_2$)$_2$), 3.15 (s, 2×$CH_3$), 3.35-3.50 (m, $CH_2$)$_3$), 3.52-3.62 ($CH_2$), 3.63-3.73 (m, (O$CH_2$$CH_2$)$_n$), 4.00 (m, $CH_2$), 5.34 (m, CH=CH), 7.84 (s, NH). $^{13}$C-NMR (125 MHz, CDCl$_3$, TMS) δ (ppm): 14.0, 22.6, 23.5, 26.0, 27.1, 29.2, 29.4, 29.5, 29.6, 29.7, 31.8, 35.7, 43.3, 50.8, 55.1, 62.1, 62.9, 68.8-71.5, 129.7, 129.8, 171.0 IR υ (cm$^{-1}$) 3406, 2924, 2856, 1647, 1466, 1349, 1290, 1097, 1037, 948.

Synthesis of Oleyl Polyoxyethylene Amidopropyl Hydroxy Sulfobetaine (OPAH)

The intermediate 4 (10.0 g, 12.76 mmol), 3-chloro-2-hydroxypropanesulfonic acid sodium salt (1) (3.13 g, 15.94 mmol), and sodium carbonate (1.35 g, 12.76 mmol) were dissolved in Ethanol:water (72:24 mL) using 0.5 L 2-necked round bottom flask joined with a condenser. The pale yellow viscous material was obtained, filtered, washed with toluene after the reaction that was continued at 85° C. for 12 hours. The viscous product was further purified using column chromatography. The column was filled with silica and ethanol was used as a mobile phase to afford surfactant OPAH (See N. Parris, J. Well, W. Linfield, Soap-based detergent formulations: XII. Alternate syntheses of surface active sulfobetaines, Journal of the American Oil Chemists' Society 53(2) (1976) 60-63; and X. F. Geng, X. Q. Hu, J. J. Xia, X. C. Jia, Synthesis and surface activities of a novel di-hydroxyl-sulfate-betaine-type zwitterionic gemini surfactants, Applied surface science 271 (2013) 284-290, each incorporated herein by reference in their entirety) as a pale yellow viscous material. $^1$H-NMR (500 MHz, CDCl$_3$, TMS) δ ppm. 0.87 (t, J=6.7 Hz, $CH_3$), 1.16-1.36 (m, ($CH_2$)$_n$), 1.51-1.61 (m, $CH_2$), 1.95-2.05 (m, ($CH_2$)$_3$), 3.22, (m, $CH_2$), 3.21 (s, 2×$CH_3$), 3.45-3.55 (m, ($CH_2$)$_2$), 3.50-3.65 (m, (O$CH_2$$CH_2$)$_n$), 4.00 (m, $CH_2$) 4.67 (m, CH), 5.34 (m, CH=CH), 7.97 (s, NH). $^{13}$C-NMR (chloroform-d, 125 MHz) δ (ppm): 14.0, 22.5, 25.9, 27.1, 29.2, 29.4, 29.5, 29.6, 29.7, 31.8, 35.8, 51.8, 55.3, 62.9, 63.5, 68.5-71.4, 129.7, 129.8, 171.2. IR υ (cm$^{-1}$) 3404, 2923, 2855, 1647, 1458, 1349, 1297, 1097, 1041, 948.

Results and Discussion

The synthesis of OPAC, OPAS, and OPAH is depicted in FIG. 10 [Y. Wang, Y. Zhang, X. Liu, J. Wang, L. Wei, Y. Feng, Effect of a Hydrophilic Head Group on Krafft Temperature, Surface Activities and Rheological Behaviors of Erucyl Amidobetaines, J. Surfactants. Deterg. 17(2) (2014) 295-301; Z. Chu, Y. Feng, A facile route towards the preparation of ultra-long-chain amidosulfobetaine surfactants, Synlett 2009(16) (2009) 2655-2658; each incorporated herein by reference in their entirety]. 3-(dimethylamino)-1-propylamine (5) was treated with glycolic acid ethoxylate oleyl ether (6) (average Mn ~700) using sodium fluoride as a catalyst at 160° C. to acquired intermediate (4). The intermediate (4) was then separately treated with sodium chloroacetate (3), 1,3-propanesultone (2), and 3-chloro-2-hydroxypropanesulfonic acid sodium salt (1) to form the corresponding OPAC, OPAS, and OPAH, respectively.

Structure Elucidation

Figure 2:
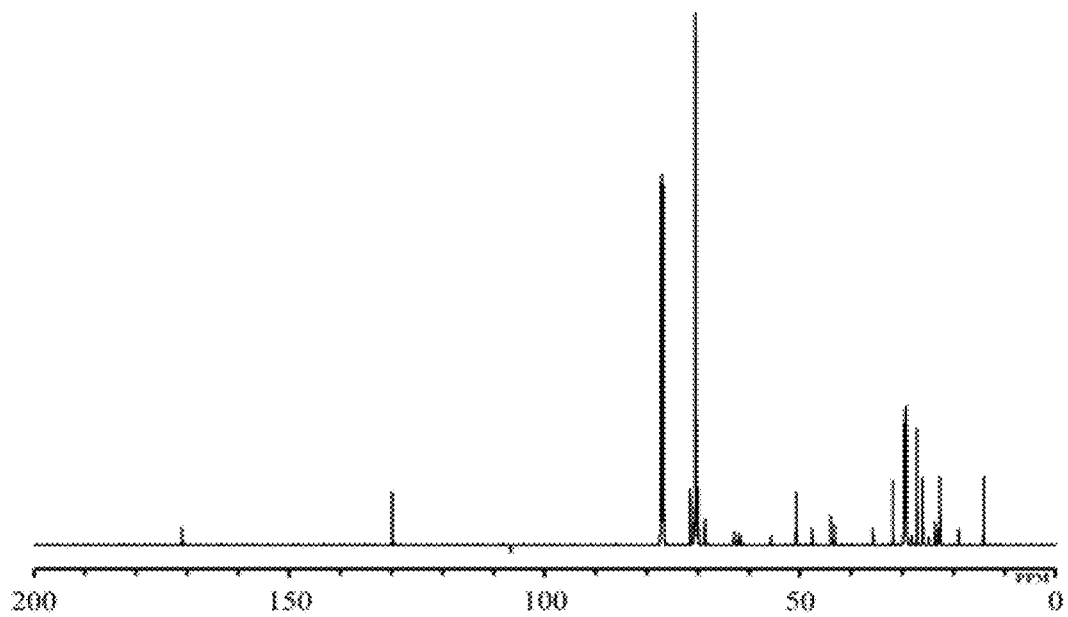
FIG. 2 illustrates the $^{13}$C NMR spectra of OPAS.
Figure 3:
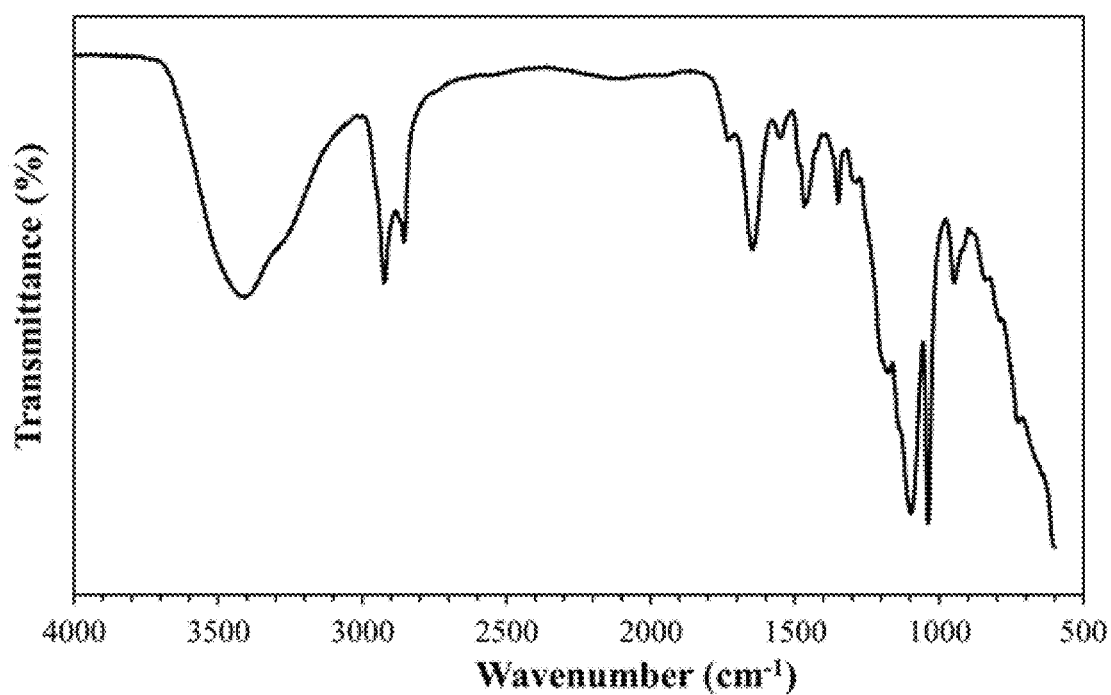
FIG. 3 is a graph illustrating the FT-IR spectra of OPAS.

The structures of all synthesized material, as well as intermediate, were confirmed using FTIR and NMR (proton, carbon-13) spectrophotometer. The structure confirmation of OPAS is presented here for example. According to proton NMR spectra of OPAS (FIG. 1), the peaks at δ 0.88 and δ 1.17-1.37 could be linked to $CH_3$ and $CH_2$ groups [($\underline{CH}_3$—($\underline{CH}_2$)$_n$—] in the hydrophobic tail of OPAS respectively. The $CH_3$ groups of quaternary ammonium headgroup [—$CH_2$—N—(CH$_3$)$_2$—$CH_2$—] could be associated with the singlet peak resonated at δ 3.15. The $CH_2$ groups of ethoxy units (—$\underline{CH}_2$—$\underline{CH}_2$—O—$\underline{CH}_2$—$\underline{CH}_2$—O—) could be related to overlapped peaks detected at δ 3.62-3.72. The peak of 2 protons at δ 5.34 could be coupled with the internal olefin (—$CH_2$—CH=CH—$CH_2$—) of surfactant tail. The amide N—H could be referred to the peak of 1 proton at δ 7.84. According to carbon-13 NMR spectra of OPAS (FIG. 2), the peaks at δ 14.0 and 22.6-35.7 could be coupled with the $CH_3$ and $CH_2$ groups [($\underline{CH}_3$—($\underline{CH}_2$)$_n$-] in the hydrophobic tail of OPAS. The $CH_3$ groups of quaternary ammonium headgroup [—$CH_2$—N—($\underline{CH}_3$)$_2$—$CH_2$-] could be associated with the peak resonated at δ 50.8. The $CH_2$ groups connected with ammonium headgroup [—$\underline{CH}_2$—N—(CH$_3$)$_2$—$\underline{CH}_2$-] could be linked with the peak observed at δ 62.1 and δ 62.9. The $CH_2$ groups of ethoxy units (—$\underline{CH}_2$—$CH_2$—O—$\underline{CH}_2$—$\underline{CH}_2$—O—) could be related to overlapped peaks detected at δ 68.8-71.5. The two peaks observed at δ 129.7 and δ 129.8 could be coupled with the two carbons of internal olefin (—$CH_2$—CH=CH—$CH_2$—) of surfactant tail. The amide carbonyl (R—C=O—NH) could be referred to the peak detected at δ 171.0. In FTIR spectra of OPAS (FIG. 3), the N—H stretching and C=O stretching of amide functionality were detected at 3406 cm$^{-1}$ and 1647 cm$^{-1}$ respectively. Asymmetric and symmetric stretching of a C—H band of hydrophobic tail of OPAS were resonated at 2923 cm$^{-1}$ and 2855 cm$^{-1}$. Ether (C—O—C) stretching bands and C—H bending vibration were identified at 1097 cm$^{-1}$ and 1466 cm$^{-1}$, respectively. Overall, FT-IR and NMR (proton, carbon-13) were matched with the structure of OPAS.

Salt Tolerance

Figure 4:
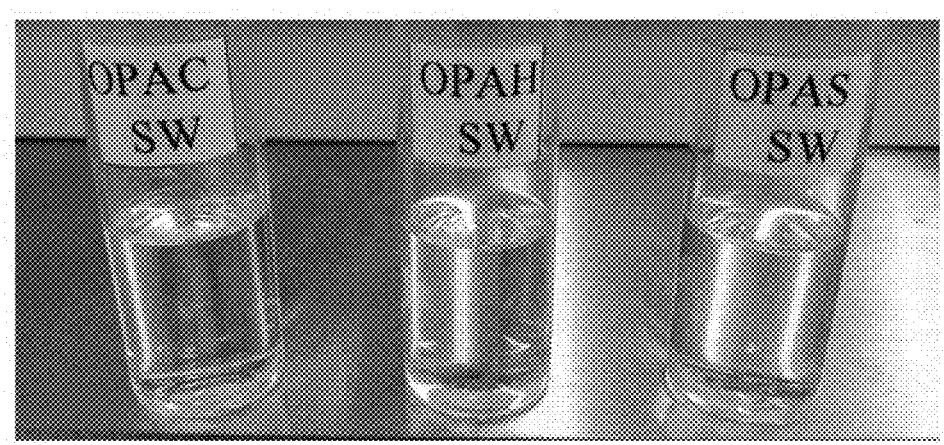
FIG. 4 is a snapshot of surfactant solutions (OPAC, OPAH, and OPAS) in seawater for 90 days at 90° C., showing no signs of precipitation or phase separation.
Figure 5:
FIG. 5 is a snapshot of surfactant solutions (OPAC, OPAH, and OPAS) in formation water for 90 days at 90° C., showing no signs of precipitation or phase separation.

Solubility and stability of the surfactants at reservoir temperature and ions are the major factors considered for its oilfield applications. Less soluble surfactants in FW and injected water (SW) are not considered for such kind of applications. Surfactants containing a long tail (≥C18) are not good candidates for oilfield applications owing to the poor solubility in FW and SW. See S. Shakil Hussain, M. A. Animashaun, M. S. Kamal, N. Ullah, I. A. Hussein, A. S. Sultan, Synthesis, characterization and surface properties of amidosulfobetaine surfactants bearing odd-number hydrophobic tail, Journal of Surfactants and Detergents 19(2) (2016) 413-420, incorporated herein by reference in its entirety. However, proper adjustment of EO groups within the surfactant structure can enhance the solubility through hydrogen bonding. This hydrogen bonding takes place between the hydrogen of water and oxygen of ethoxy group. See C. Negin, S. Ali, Q. Xie, Most common surfactants employed in chemical enhanced oil recovery, Petroleum 3(2) (2017) 197-211, incorporated herein by reference in its entirety. The solubility and salt tolerance experiments of OPAC, OPAS, and OPAH were done at 90° C. for 90 days in FW, SW, and DW. All surfactants (OPAC, OPAS, and OPAH) showed excellent solubility in FW, SW, and DW and no apparent insoluble surfactants were detected. The solutions of OPAC, OPAS, and OPAH in FW, SW, and DW remained transparent for 90 days at 90° C. and no precipitation or phase separation was detected (FIGS. 4 and 5) which demonstrated excellent solubility and salt tolerance of the synthesized OPAC, OPAS, and OPAH.

Thermal Stability

Figure 6:
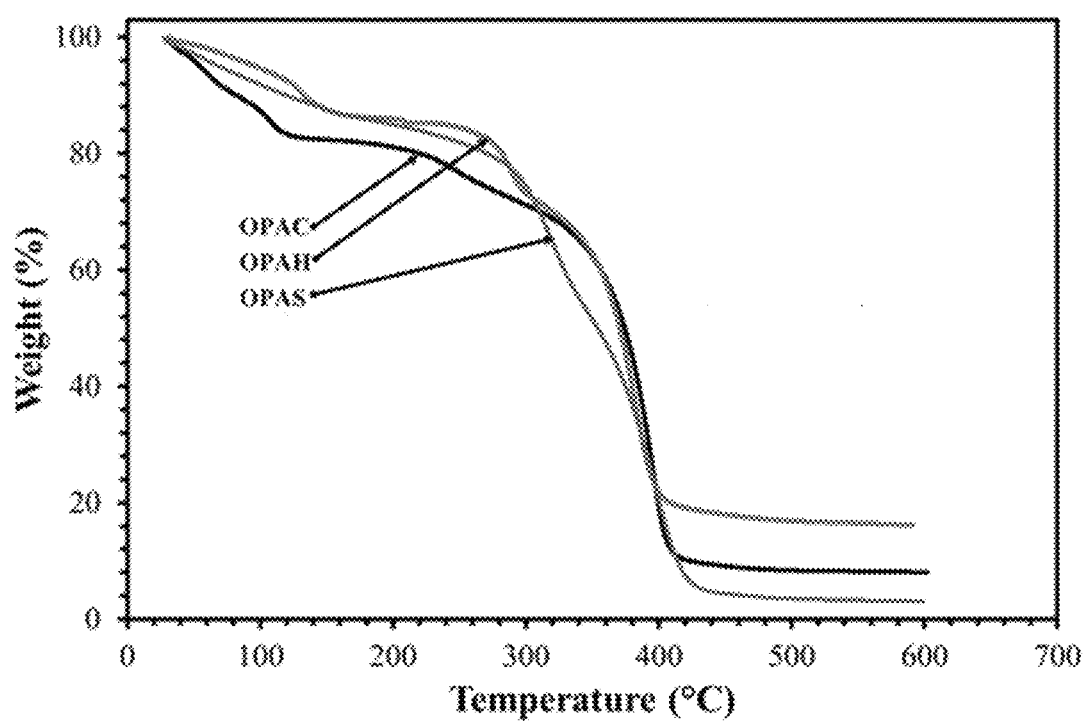
FIG. 6 is a TGA graph of OPAC, OPAS, and OPAH.

Thermal stability of any injected chemical at reservoir conditions is the prerequisite for its oilfield application. The residence time for surfactants in oil reservoir is very long and the high temperature of oil reservoir (≥90° C.) can lead to surfactant decomposition. The heat stabilities of the OPAC, OPAS, and OPAH surfactants were studied using TGA analysis. According to TGA data (FIG. 6), all three surfactants (OPAC, OPAS, and OPAH) found to be stable almost up to 300° C. The initial loss in weight was 30%, 29%, and 25% for OPAC, OPAH, and OPAS, respectively. This weight loss is associated with the water and solvent. The big weight loss was noticed at 312° C., 307° C., and 295° C. for OPAC, OPAH, and OPAS respectively which is quite higher than the existing oilfield temperatures (≥90° C.).

Surface Tension

Figure 7:
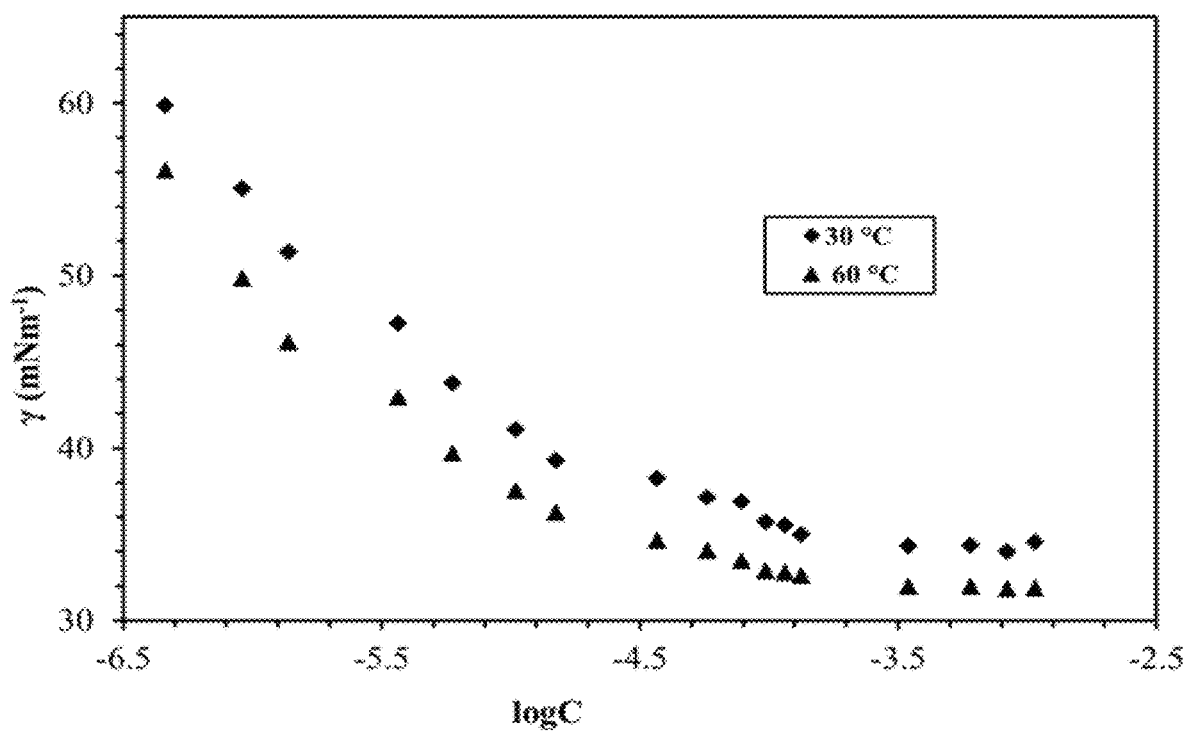
FIG. 7 is a graph illustrating the surface properties of OPAC at various concentrations at 30° C. and 60° C. in water.
Figure 8:
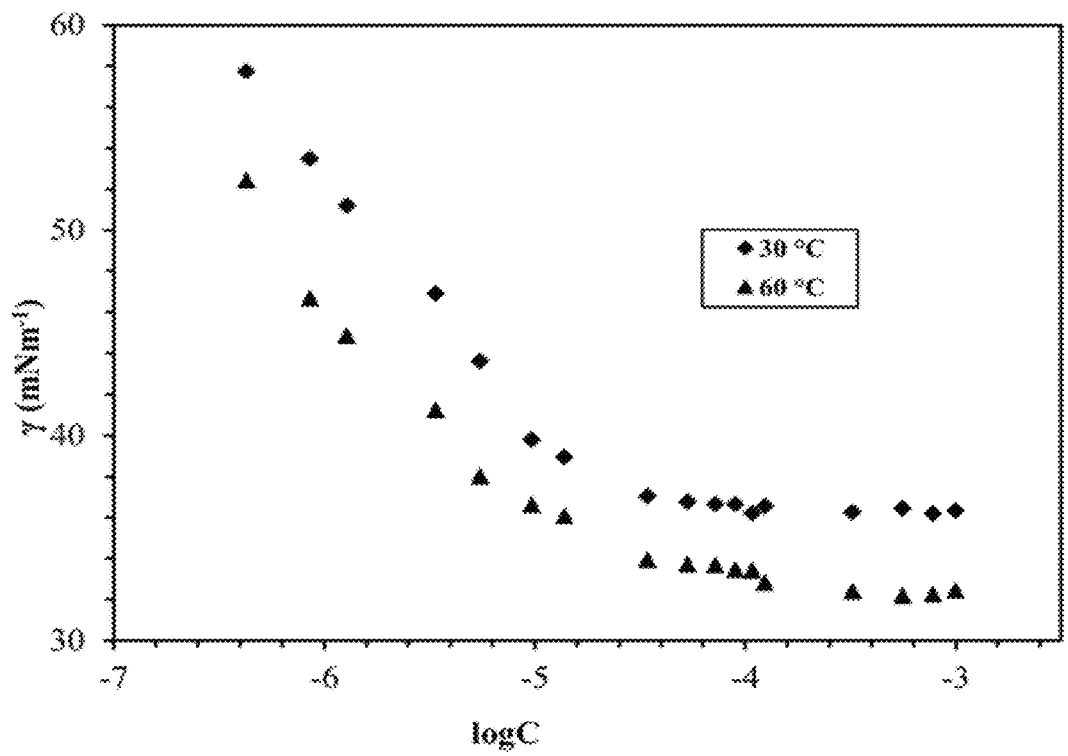
FIG. 8 is a graph illustrating the surface properties of OPAS at various concentrations at 30° C. and 60° C. in water.
Figure 9:
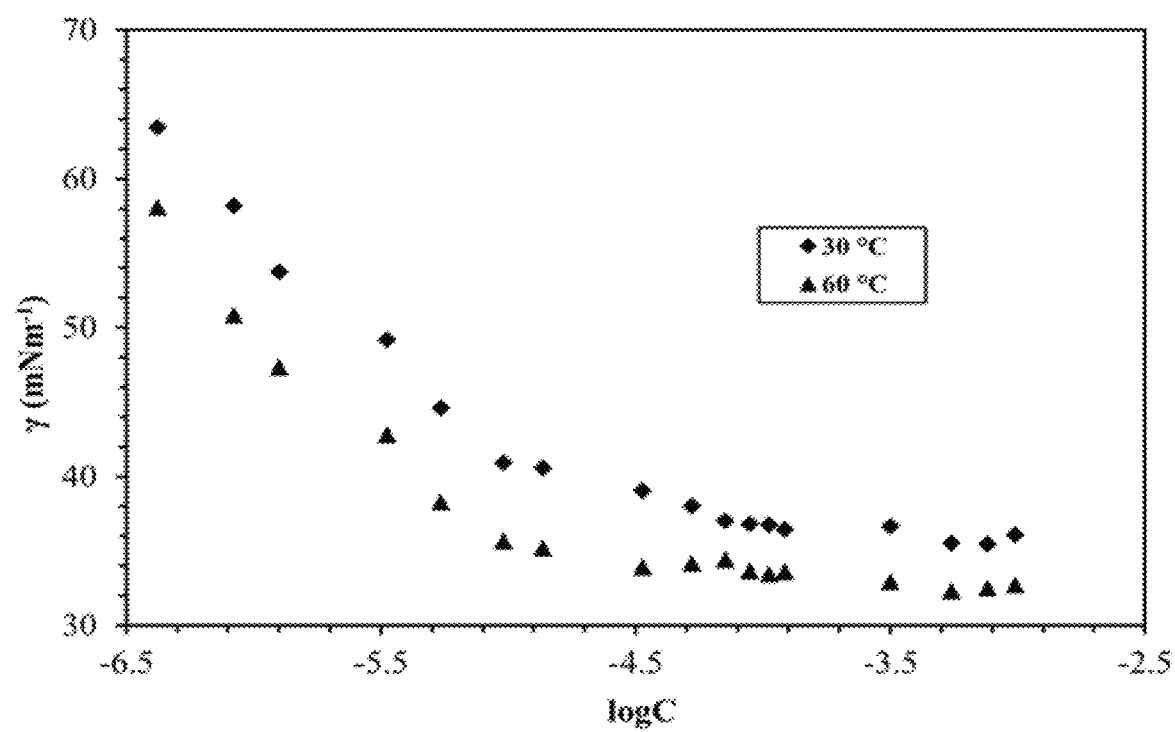
FIG. 9 is a graph illustrating the surface properties of OPAH at various concentrations at 30° C. and 60° C. in water.

The surface properties of the synthesized surfactants were analyzed at 30° C. and 60° C. and the data is presented in FIGS. 7-9 and summarized in Table 2. The surface tension data was further used to determine other surface properties such as cmc. The surface tension of OPAC, OPAS, and OPAH showed similar behavior by varying temperature and concentration. The reduction in surface tension was noticed upon increasing surfactant concentration until the break-point which is also called cmc. At higher concentrations (>cmc), the change in surface tension associated with surfactant concentration was negligible. The surface tension reduced by increasing the temperature and this behavior was noted for all surfactants. The surface tension reduction caused by temperature was related to a reduction in hydrophilic nature of surfactant because of hydrogen bond breading. See G. H. Sayed, F. M. Ghuiba, M. I. Abdou, E. A. A. Badr, S. M. Tawfik, N. A. M. Negm, Synthesis, surface, thermodynamic properties of some biodegradable vanillin-modified polyoxyethylene surfactants, Journal of Surfactants and Detergents 15(6) (2012) 735-743; and L.-J. Chen, S.-Y. Lin, C.-C. Huang, E.-M. Chen, Temperature dependence of critical micelle concentration of polyoxyethylenated non-ionic surfactants, Colloids and Surfaces A: Physicochemical and Engineering Aspects 135(1-3) (1998) 175-181, each incorporated herein by reference in their entirety.

Hydrogen bond breaking may result in separation of surfactant molecule from the water phase and adsorb at the interface which promotes micellization and results in a decrease of surface tension. The cmc and surface tension at cmc ($\gamma_{cmc}$) reduced upon increasing temperature for all surfactants (OPAC, OPAS, and OPAH). The change in the head group of the surfactants also affect the surface properties. The maximum cmc ($3.46 \times 10^{-4}$) was noted for the surfactant-containing carboxylate headgroup (OPAC). The surfactant-containing hydroxy sulfonate headgroup (OPAH) showed the least cmc ($3.35 \times 10^{-5}$ mol L$^{-1}$). Similarly, the surfactant-containing sulfonate headgroup (OPAS) showed the highest $\gamma_{cmc}$ while the OPAC showed the least $\gamma_{cmc}$. The cmc and $\gamma_{cmc}$ of OPAS and OPAH are closer to each other compared to the OPAC. The $\pi_{cmc}$ value increased by increasing the temperature and maximum $\pi_{cmc}$ was observed by using OPAC which suggests that the OPAC has more capability to reduce the surface tension but at comparatively higher concentration is required due to high cmc. The maximum surface excess ($\Gamma_{max}$, moles at the interface per unit area) of all surfactants decreased with temperature, however, OPAC showed the least value of maximum surface access at both temperatures (30° C. and 60° C.). The minimum surface area per molecule also changes by changing the headgroup and temperature. The minimum area per molecules ($A_{min}$) slightly increased by increasing the temperature and OPAC showed maximum surface area per molecule. Thus, the surface properties data indicates that the surface properties change with temperature and by varying the head group.

TABLE 2

Surface properties of OPAC, OPAS, and OPAH

| Surfactant | T (° C.) | cmc (mol L$^{-1}$) | $\gamma_{cmc}$ (mN m$^{-1}$) | $\pi_{cmc}$ (mN/m) | $\Gamma_{max} \times 10^6$ (mol m$^{-2}$) | $A_{min}$ (nm$^2$) |
|---|---|---|---|---|---|---|
| OPAC | 30 | $3.46 \times 10^{-4}$ | 34.67 | 37.33 | 1.70 | 0.97 |
| OPAC | 60 | $9.70 \times 10^{-5}$ | 32.24 | 39.76 | 1.58 | 1.04 |
| OPAH | 30 | $7.10 \times 10^{-5}$ | 36.89 | 34.96 | 2.66 | 0.62 |
| OPAH | 60 | $3.35 \times 10^{-5}$ | 33.68 | 38.07 | 2.33 | 0.71 |
| OPAS | 30 | $3.66 \times 10^{-5}$ | 37.04 | 35.59 | 2.15 | 0.77 |
| OPAS | 60 | $3.41 \times 10^{-5}$ | 33.74 | 38.26 | 1.64 | 1.01 |

Therefore, zwitterionic surfactants containing EO units and an unsaturated tail possess excellent solubility in oilfield water and high heat stability. Various ionic headgroups influence the surface and thermal behavior of betaine-based surfactants. All three surfactants (OPAC, OPAS, and OPAH) were found to be soluble in simulated SW, and FW and no apparent insoluble surfactants were observed up to 90 days at 90° C. The presence of EO units increase the hydrophilicity of the synthesized surfactants and makes them more soluble in high salinity brine. The TGA graph showed excellent heat stability and the decomposition temperatures of the surfactants were in the order of OPAC (312° C.)>OPAH (307° C.>OPAS (295° C.) which is higher than the actual oilfield temperature (≥90° C.). TGA results revealed that the nature of head group has tiny effect on the thermal stabilities. The cmc values of OPAC, OPAS, and OPAH were reduced upon enhancing the temperature by following the order OPAH<OPAS<OPAC. The high CMC value of OPAC may be due to the high hydrophilicity of the molecule. The OPAC has one methylene group between positive and negative ion pair of the molecule which make it more hydrophilic. Moreover, OPAH with extra hydroxy group has slightly lower CMC than OPAS and OPAC due to decrease in repulsion between ionic head groups leading to a lower CMC. Similarly, the $\gamma_{cmc}$ values of OPAC, OPAS, and OPAH also decreased by increasing temperature and the order of reduction was OPAC<OPAH<OPAS. However, the change in the $\gamma_{cmc}$ values with temperature was not significant. The zwitterionic surfactants containing EO units and unsaturated tail showed superior properties such as great salt tolerance, outstanding thermal stability, and higher surface characteristics which make them an appropriate candidate for severe reservoir conditions.

The invention claimed is:

1. A method of fracking a subterranean geologic formation, comprising:
   injecting an oil and gas well servicing fluid into an oil and gas well in the subterranean geologic formation,
   wherein the injecting is at a pressure above the fracture point of the subterranean geologic formation;
   wherein the oil and gas well servicing fluid comprises:
   an aqueous base fluid; and
   a surfactant of formula (I)

(I)

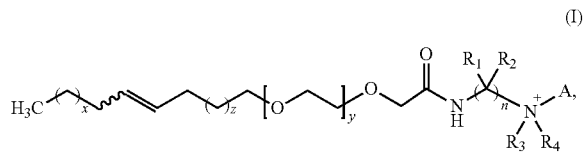

wherein:
each of $R_1$ and $R_2$ are independently H or an optionally substituted $C_1$ to $C_6$ alkyl,
$R_3$ and $R_4$ are independently an optionally substituted $C_1$ to $C_6$ alkyl;
x is 6;
y is an integer in a range of from 7 to 10;
z is 6;
n is an integer in a range of from 3 to 4;
A is an anionic headgroup selected from the group consisting of

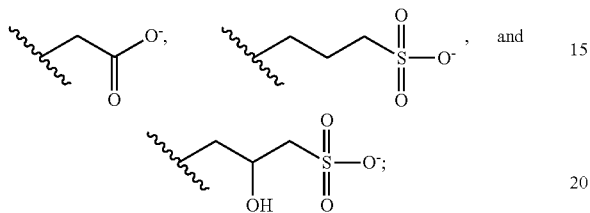

wherein the oil and gas well servicing fluid has a total dissolved solids content in a range of from 50,000 to 350,000 ppm,
wherein the surfactant is present in a range of from 0.045 to 2 wt. %, relative to a total weight of the oil and gas well servicing fluid,
wherein the surfactant has a number average molecular weight in a range of from 600 to 1200 g/mol, and
wherein, during the injecting, the surfactant has a concentration in a range of from $3 \times 10^{-5}$ to $5 \times 10^{-4}$ M.

2. The method of claim 1, wherein each of $R_1$ and $R_2$ are independently a hydrogen, or a methyl.

3. The method of claim 1, wherein each of $R_1$ and $R_2$ are a hydrogen.

4. The method of claim 1, wherein $R_3$ and $R_4$ are independently selected from the group consisting of a methyl, an ethyl, and an isopropyl.

5. The method of claim 1, wherein $R_3$ and $R_4$ are a methyl.

6. The method of claim 1, wherein y is 8.

7. The method of claim 1, wherein y is 9.

8. The method of claim 1, wherein n is 3.

9. The method of claim 1, wherein A is

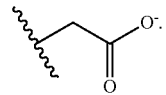

10. The method of claim 1, wherein A is

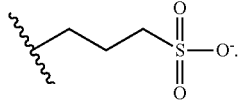

11. The method of claim 1, wherein A is

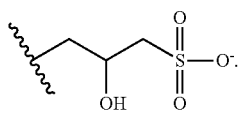

12. The method of claim 1, wherein the carbon-carbon double bond present in formula (I) is in a cis-double bond configuration.

13. The method of claim 1, wherein the surfactant is selected from the group consisting of

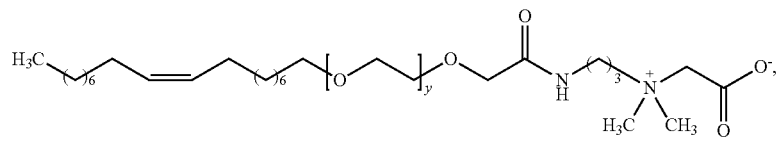

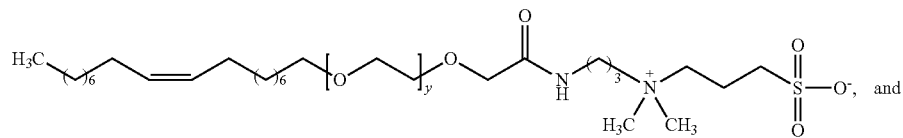

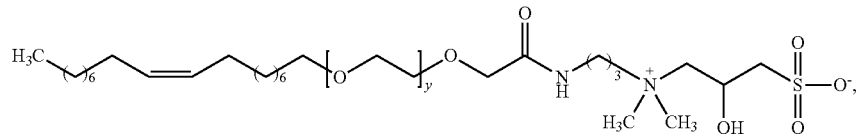

wherein in each structure y is 8 or 9.

14. The method of claim 1, wherein the surfactant is present in a range of from 0.05 to 0.1 wt. % relative to a total weight of the oil and gas well servicing fluid.

15. The method of claim 1, wherein the subterranean geologic formation has a temperature in a range of from 30 to 150° C.

* * * * *